(12) United States Patent
Bourzat et al.

(10) Patent No.: US 6,444,825 B1
(45) Date of Patent: Sep. 3, 2002

(54) PROCESS FOR THE PREPARATION OF AN OXAZOLIDINECARBOXYLIC ACID WHICH IS USEFUL FOR PREPARING THERAPEUTICALLY ACTIVE TAXOIDS

(75) Inventors: Jean-Dominique Bourzat, Vincennes; Alain Commerçon, Vitry-sur-Seine, both of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 08/564,345

(22) PCT Filed: Jun. 15, 1994

(86) PCT No.: PCT/FR94/00713
§ 371 (c)(1),
(2), (4) Date: Dec. 14, 1995

(87) PCT Pub. No.: WO94/29284
PCT Pub. Date: Dec. 22, 1994

(30) Foreign Application Priority Data

Jun. 16, 1993 (FR) ............................................. 93 07240

(51) Int. Cl.[7] ................... C07D 263/02; C07D 403/02; C07D 413/02
(52) U.S. Cl. ...................... 548/215; 548/216; 548/230; 546/208; 544/137; 544/369
(58) Field of Search ................................ 548/215, 216, 548/230; 570/206; 546/208; 544/137, 369

(56) References Cited

U.S. PATENT DOCUMENTS

| | | | | |
|---|---|---|---|---|
| 4,240,987 A | * | 12/1980 | Martin et al. ................ | 570/206 |
| 4,924,012 A | * | 5/1990 | Colin et al. .................. | 549/510 |
| 5,476,954 A | * | 12/1995 | Bourzat et al. ............. | 548/215 |
| 5,532,388 A | * | 7/1996 | Bouchard et al. ........... | 548/215 |
| 5,556,877 A | * | 9/1996 | Bouchard et al. ........... | 549/510 |
| 5,616,739 A | * | 4/1997 | Mas et al. ................... | 549/510 |
| 5,621,121 A | * | 4/1997 | Commercon et al. ....... | 549/510 |

FOREIGN PATENT DOCUMENTS

WO    WO 92/09589    6/1992

* cited by examiner

Primary Examiner—Brenda Coleman
(74) Attorney, Agent, or Firm—Finnegan, Henderson, Farabow, Garrett & Dunner LLP

(57) ABSTRACT

A method for preparing an oxazolidinecarboxylic acid of general formula (I), which is useful for preparing therapeutically active taxoids of general formula (III), from an oxazolidinecarboxylic acid of general formula (II). In formulae (I), (II) and (III), R is a hydrogen atom or an acetyl radical; $R_1$ is a benzyl radical or a radical of the general formula $R_2$—O—CO—, wherein $R_2$ is an optionally substituted alkyl radical, alkenyl, alkynyl, cycloalkyl, cycloalkenyl, bicycloalkyl, phenyl or heterocyclyl; each of $R_3$ and $R_4$, which are the same or different, is hydrogen, alkyl, alkoxy, optionally substituted aryl or optionally substituted aralkyl, or together they form a 4–7 membered ring; $R_5$ is alkenyl, alkynyl, phenyl, formyl, alkanoyl, aroyl, hydroxymethyl, carboxy or alkyloxycarbonyl; and R' is a hydrogen atom or an alkali or alkaline-earth metal atom or an alkyl radical with 1–4 carbon atoms optionally substituted by phenyl radical.

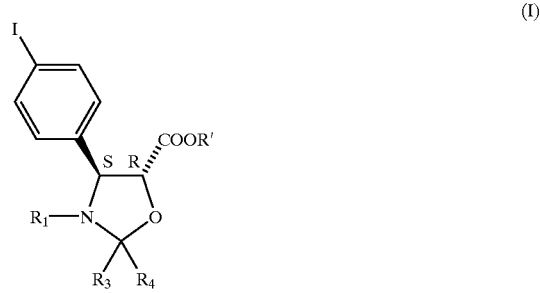

(I)

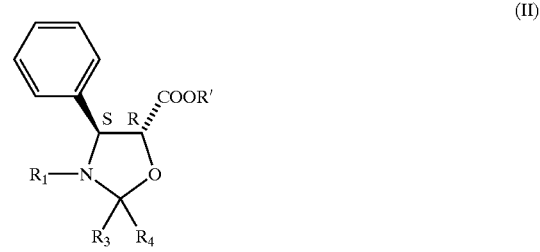

(II)

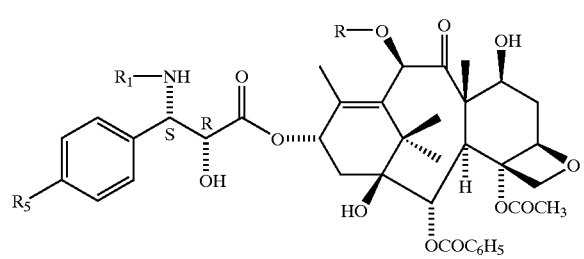

(III)

12 Claims, No Drawings

PROCESS FOR THE PREPARATION OF AN OXAZOLIDINECARBOXYLIC ACID WHICH IS USEFUL FOR PREPARING THERAPEUTICALLY ACTIVE TAXOIDS

This application is a national stage entry under 35 USC §371 of PCT/FR94/00713, filed Jun. 15, 1994.

The present invention relates to a process for the preparation of an oxazolidinecarboxylic acid or derivatives thereof, of general formula:

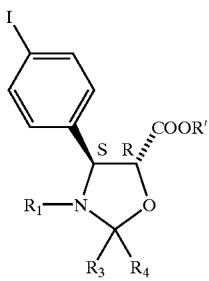

(I)

from an acid or derivatives thereof, of general formula:

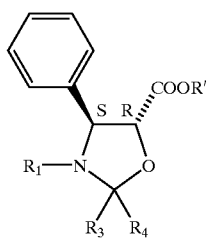

(II)

In the formulae (I) and (II),

R' represents a hydrogen atom or an alkali metal or alkaline-earth metal atom or an alkyl radical containing 1 to 4 carbon atoms optionally substituted with a phenyl radical, $R_1$ represents a benzoyl radical or a radical $R_2$—O—CO— in which $R_2$ represents:

a straight or branched alkyl radical containing 1 to 8 carbon atoms, an alkenyl radical containing 3 to 6 carbon atoms, a cycloalkyl radical containing 3 to 6 carbon atoms or a cycloalkenyl radical containing 4 to 6 carbon atoms, these radicals being optionally substituted with one or more substituents chosen from halogen atoms and hydroxyl radicals, alkyloxy radicals containing 1 to 4 carbon atoms, dialkylamino radicals in which each alkyl portion contains 1 to 4 carbon atoms, piperidino, morpholino and 1-piperazinyl (optionally substituted at position 4 with an alkyl radical containing 1 to 4 carbon atoms or with a phenylalkyl radical in which the alkyl portion contains 1 to 4 carbon atoms) radicals, cycloalkyl radicals containing 4 to 6 carbon atoms, alkenyl radicals containing 4 to 6 carbon atoms, phenyl, cyano and carboxyl radicals or alkyloxycarbonyl radicals in which the alkyl portion contains 1 to 4 carbon atoms, or a phenyl radical optionally substituted with one or more atoms or radicals chosen from halogen atoms and alkyl radicals containing 1 to 4 carbon atoms or alkyloxy radicals containing 1 to 4 carbon atoms, or a saturated or unsaturated nitrogen-containing 5- or 6-membered heterocyclic radical optionally substituted with one or more alkyl radicals containing 1 to 4 carbon atoms, $R_3$ and $R_4$, which may be identical or different, represent a hydrogen atom or an alkyl radical containing 1 to 4 carbon atoms or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably a phenyl radical optionally substituted with one or more alkoxy radicals containing 1 to 4 carbon atoms, or alternatively $R_3$ represents an alkoxy radical containing 1 to 4 carbon atoms or a trihalomethyl radical such as trichloromethyl or a phenyl radical. substituted with a trihalomethyl radical such as trichloromethyl and $R_4$ represents a hydrogen atom, or alternatively $R_3$ and $R_4$ form, together with the carbon atom to which they are attached, a 4- to 7-membered ring.

The acid of general formula (I) is particularly useful for preparing the therapeutically active taxoids of general formula:

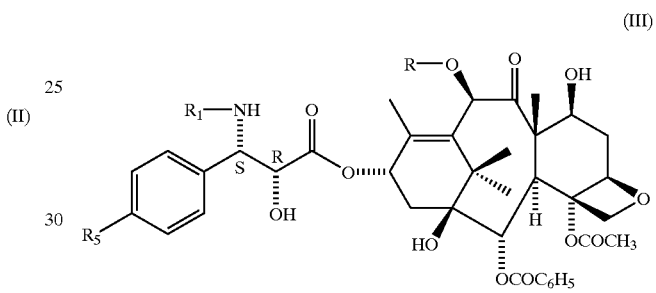

(III)

in which:

R represents a hydrogen atom or the acetyl radical, $R_1$ is defined as above, and $R_5$ represents an iodine atom or an alkenyl radical containing 2 to 8 carbon atoms optionally substituted with a phenyl radical, an alkynyl radical containing 2 carbon atoms or a phenyl, formyl, alkanoyl, aroyl, hydroxymethyl, carboxyl or alkoxycarbonyl radical.

According to Application PCT WO 9209589, the preparation of a product of general formula (III) requires the use of an oxazolidinecarboxylic acid of general formula:

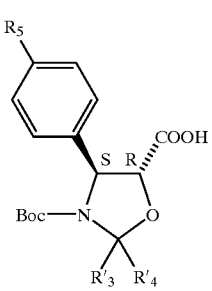

(IV)

in which $R_5$ is defined as above, $R'_3$ and $R'_4$, which may be identical or different, represent an alkyl radical containing 1 to 4 carbon atoms optionally substituted with one or more aryl (phenyl) radicals or represent an aryl (phenyl) radical, or alternatively R'$_3$ and R'$_4$ form, together with the carbon atom to which they are attached, a 4- to 7-membered ring, and Boc represents the t-butoxycarbonyl radical, which is obtained from an aldehyde of general formula:

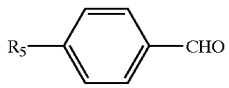

(V)

in which R$_5$ is defined as above, which, depending on the meanings of R$_5$, is not always easily accessible.

According to the invention, the product of general formula (I) in which R' represents an alkyl radical optionally substituted with a phenyl radical is obtained by iodination, according to the usual methods, of a product of general formula (II) in which R' represents an alkyl radical optionally substituted with a phenyl radical.

The iodination may generally be carried out either using iodine in the presence of bis(trifluoroacetoxy)iodobenzene by working in an organic solvent such as a halogenated aliphatic hydrocarbon like dichloromethane at a temperature between 0 and 50° C., or alternatively by the action of iodine in the presence of ammonium cerium nitrate in acetic acid or methanol, or alternatively by the action of iodine in the presence of silver trifluoroacetate, or alternatively by the action of N-iodosuccinimide in the presence of hydroxy (tosyloxy)iodobenzene (Koser's reagent) in methanol, or alternatively by the action of benzyltrimethylammonium dichloroiodide in the presence of zinc chloride in acetic acid.

The product of general formula (I) for which R' represents a hydrogen atom may be obtained by saponification of a product of general formula (I) in which R' represents an alkyl radical optionally substituted with a phenyl radical.

The product of general formula (II) in which R' represents an alkyl radical optionally substituted with a phenyl radical, R$_3$ and R$_4$ are defined as above, may be obtained by reacting a product of general formula:

(VI)

in which R$_3$ and R$_4$ are defined as above in the form of a dialkyl acetyl or an alkyl enol ether, with an ester of general formula:

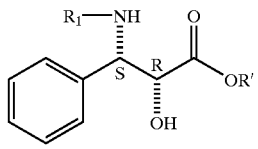

(VII)

in which R$_1$ and R' are defined as above, which may be obtained under the conditions described in the Application PCT WO 9209589, corresponding U.S. Pat. No. 5,476,954.

The product of general formula (I) may be converted to a product of general formula (III) according to one of the following methods:

1) after replacing the iodine atom of the product of general formula (I), in which R' represents an alkyl radical optionally substituted with a phenyl radical, with an alkenyl radical containing 2 to 8 carbon atoms optionally substituted with a phenyl radical, an alkynyl radical containing 2 carbon atoms or a phenyl, formyl, alkanoyl, aroyl, hydroxymethyl, carboxyl or alkoxycarbonyl radical according to the known methods, and saponification, the product obtained of general formula:

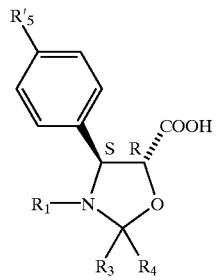

(VIII)

in which R$_1$, R$_3$ and R$_4$ are defined as above, and R'$_5$ represents an alkenyl radical optionally substituted with a phenyl radical or an alkynyl, phenyl, alkanoyl, aroyl, formyl, hydroxymethyl, carboxyl or alkoxycarbonyl radical, or a derivative of the acid of general formula (VIII), is condensed with a protected baccatin III of general formula:

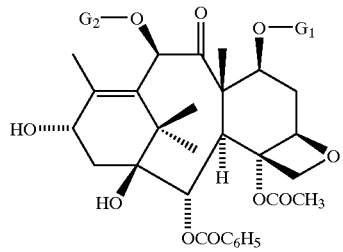

(IX)

in which G$_1$ represents a protecting group for the hydroxyl function and G$_2$ represents an acetyl radical or a protecting group for the hydroxyl function, in order to obtain a product of general formula:

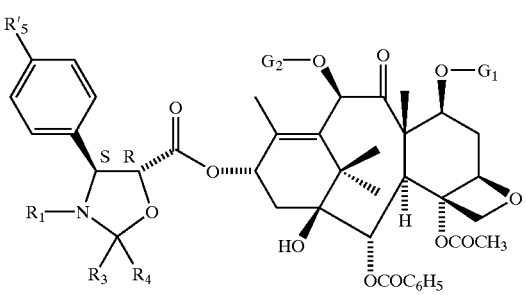

(X)

in which R$_1$, R$_3$, R$_4$, R'$_5$, G$_1$ and G$_2$ are defined as above, in which the protecting groups represented by G$_1$ and G$_2$ are replaced by hydrogen atoms by passing, depending on the meanings of R$_3$ and R$_4$, via an intermediate product of general formula:

(XI)

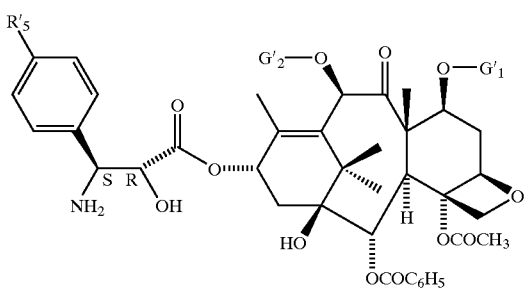

in which R'₅ is defined as above, G'₁ represents a hydrogen atom or a protecting group for the hydroxyl function and G'₂ represents a hydrogen atom or an acetyl radical or a protecting group for the hydroxyl function, in which the amine function is acylated before replacing the protecting groups G'₁ and, where appropriate, G'₂ by hydrogen atoms.

2) the product of general formula (I), in which R' represents a hydrogen atom, is condensed with a protected baccatin III of general formula (IX) in order to give a product of general formula:

(XII)

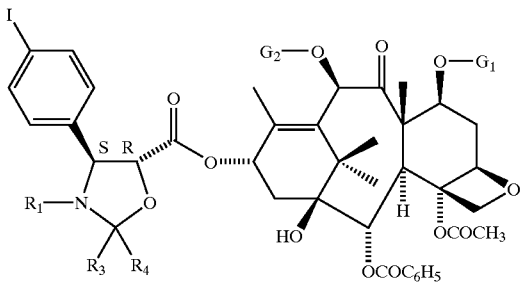

in which R₁, R₃, R₄, G₁ and G₂ are defined as above, in which the protecting groups represented by G₁ and G₂ are replaced by hydrogen atoms by passing, depending on the meanings of R₃ and R₄, via an intermediate product of general formula:

(XIII)

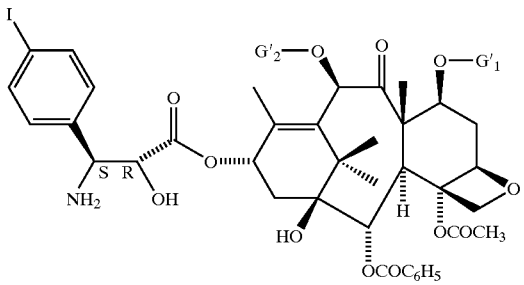

in which G'₁ and G'₂ are defined as above, in which the amine function is acylated before replacing the groups G'₁ and, where appropriate, G'₂ by hydrogen atoms and then the iodine atom by a radical R'₅ as defined above.

3) a product of general formula (III) may also be obtained from a product of general formula (III) prepared according to the sequence described above in 1) by any method which allows a substituent R'₅ to be converted into a different substituent R'₅, for example, a product of general formula (III) in which R'₅ represents a vinyl radical may be converted, by ozonolysis, to a different product of general formula (III) in which R'₅ represents a formyl radical.

Depending on the meanings of R'₅, the product of general formula (VIII), in ester form, may be prepared according to known methods.

The product of general formula (VIII), in ester form, for which R'₅ represents an alkenyl radical optionally substituted with a phenyl radical, may be obtained by reacting a boronic acid of general formula:

(XIV)

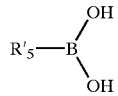

in which R'₅ is defined as above, with a product of general formula (I) in which R' represents an alkyl radical optionally substituted with a phenyl radical.

The reaction is generally carried out in the presence of a catalyst such as palladium combined with a ligand such as triphenylphosphine by working in an organic solvent such as an aromatic hydrocarbon (benzene, toluene or xylene) at a temperature between 0 and 100° C.

The product of general formula (VIII), in ester form, for which R'₅ represents an alkynyl radical, may be obtained by reacting an acetylene derivative of general formula:

$$H—C≡C—Si(R")_3 \quad (XV)$$

in which R" represents an alkyl radical containing 1 to 4 carbon atoms, with a product of general formula (I) in which R' represents an alkyl radical optionally substituted with a phenyl radical.

The reaction is generally first of all carried out in the presence of a catalyst consisting of palladium combined with a ligand such as triphenylphosphine and a copper salt such as cuprous iodide, by working in a basic organic solvent such as diethylamine at a temperature in the region of 20° C., and then in the presence of a desilylating agent such as silver nitrate in a protic solvent or of silver nitrate in an organic solvent such as an aliphatic alcohol like ethanol, in order to displace the silyl residue.

The product of general formula (VIII), in ester form, for which R'₅ represents a formyl, acyl or aroyl radical, may be obtained by ozonolysis of a product of general formula (VIII), in ester form, in which R'₅ represents an alkenyl radical optionally substituted with a phenyl radical.

The ozonolysis is generally carried out in an organic solvent such as a dichloromethane/methanol mixture at a temperature lower than −50° C.

The product of general formula (VIII), in ester form, for which R'₅ represents a hydroxymethyl radical, may be obtained by reduction, using an alkali metal cyanoborohydride, of a product of general formula (VIII) for which R'₅ represents a formyl radical.

The product of general formula (VIII), in ester form, for which R'₅ represents a carboxyl radical, may be obtained by oxidation, for example using sodium perborate, of a product of general formula (VIII) in which R'₅ represents a formyl radical.

The product of general formula (VIII), in ester form, for which R'₅ represents an alkoxycarbonyl radical, may be obtained, for example, by reacting an N,N- dimethylformamide acetal with a product of general formula (VIII) in which R'₅ represents a carboxyl radical.

The saponification of a product of general formula (I) or of a product of general formula (VIII), in ester form, in which R' represents an alkyl radical optionally substituted with a phenyl radical, to a product of general formula (I) or a product of general formula (VIII), in which R' represents a hydrogen atom, may be carried out using an inorganic base such as lithium hydroxide, by working in an aqueous-alcoholic medium such as a water/methanol mixture.

When, in the product of general formula (III), R₅ represents an iodine atom, its replacement by a radical R'₅, is carried out under the conditions described above, in order to convert a product of general formula (I) to a product of general formula (VIII)

The esterification of the protected baccatin III using an acid of general formula (I) or an acid of general formula (VIII) or a derivative such as a halide, an anhydride or a mixed anhydride may be carried out under the following conditions:

1) esterification using an acid of general formula (I) or (VIII) may be carried out in the presence of a condensing agent (carbodiimide, reactive carbonate) and an activating agent (amino pyridine) in an organic solvent (ethers, esters, ketones, nitrites, aliphatic hydrocarbons, halogenated aliphatic hydrocarbons, aromatic hydrocarbons) at a temperature between −10 and 90° C.

2) esterification may also be performed by using the acid of general formula (I) or (VIII) in anhydride form in the presence of an activating agent (aminopyridine) in an organic solvent (ethers, esters, ketones, nitriles, aliphatic hydrocarbons, halogenated aliphatic hydrocarbons, aromatic hydrocarbons) at a temperature between 0 and 90° C.

3) esterification may also be performed by using the acid of general formula (I) or (VIII) in halide form or in an anhydride form with an aliphatic or aromatic acid, optionally prepared in situ, in the presence of a base (tertiary aliphatic amine) by working in an organic solvent (ethers, esters, ketones, nitriles, aliphatic hydrocarbons, halogenated aliphatic hydrocarbons, aromatic hydrocarbons) at a temperature between 0 and 80° C.

Replacement of the protecting groups R₃, R₄, G₁ and G₂ in the products of general formulae (X) or (XII) by hydrogen atoms may be carried out by working, depending on the meanings of R₃ and R₄, in the following way:

1) when R₃ represents a hydrogen atom or an alkoxy radical containing 1 to 4 carbon atoms or an optionally substituted aryl radical and R₄ represents a hydrogen atom, the product of general formula (X) or (XII) is treated in an acidic medium in order to obtain a product of general formula:

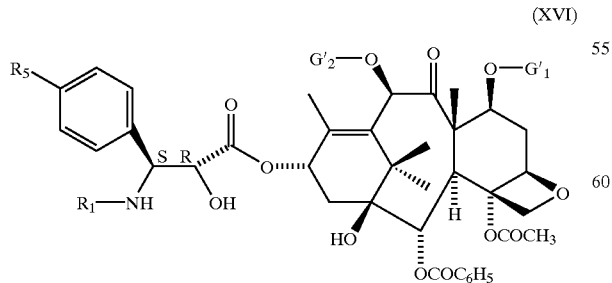

(XVI)

in which R₁ and R₅ are defined as above, G'₁ represents a hydrogen atom or a protecting group for the hydroxyl function and G'₂ represents a hydrogen atom or an acetyl radical or a protecting group for the hydroxyl function, in which the protecting groups G'₁ and G'₂ are, if necessary, replaced by hydrogen atoms in order to obtain a product of general formula (III).

The deprotection of the side chain of the product of general formula (X) or (XII) may be carried out in the presence of an inorganic acid (hydrochloric acid or sulphuric acid) or an organic acid (acetic acid, methanesulphonic acid, trifluoromethanesulphonic acid or p-toluenesulphonic acid), used alone or mixed, by working in an organic solvent chosen from alcohols (methanol, ethanol or isopropanol), ethers (tetrahydrofuran, diisopropyl ether or methyl t-butyl ether), esters (ethyl acetate, isopropyl acetate or n-butyl acetate), aliphatic hydrocarbons (pentane, hexane or heptane), halogenated aliphatic hydrocarbons (dichloromethane or 1,2-dichloroethane), aromatic hydrocarbons (benzene, toluene or xylenes) and nitriles (acetonitrile) at a temperature between −10 and 60° C., preferably between 15 and 30° C. The acid may be used in a catalytic or stoichiometric amount or in excess.

The deprotection may also be performed under oxidizing conditions by using, for example, ammonium cerium IV nitrate in an acetone/water mixture or 2,3-dichloro-5,6-dicyano-1,4-benzoquinone in water.

The deprotection may also be performed under reducing conditions, for example by hydrogenolysis in the presence of a catalyst.

The radicals G₁ and G₂, as well as G'₁ and G'₂, when they represent a protecting group for the hydroxyl function, are preferably 2,2,2-trichloroethoxycarbonyl or 2-(2-trichloromethylpropoxy)carbonyl radicals or trialkylsilyl, dialkylarylsilyl, alkyldiarylsilyl or triarylsilyl radicals in which the alkyl portions contain 1 to 4 carbon atoms and the aryl portions are preferably phenyl radicals.

Replacement by hydrogen atoms, in the product of general formula (XVI) of the protecting groups G'₁ and, where appropriate, G'₂ representing a silyl radical, may be carried out simultaneously with the deprotection of the side chain.

The replacement by hydrogen atoms, in the product of general formula (XVI), of the protecting groups G'₁ and G'₂ representing a 2,2,2-trichloroethoxycarbonyl or 2-(2-trichloromethylpropoxy)carbonyl radical, is carried out by zinc, optionally combined with copper, in the presence of acetic acid at a temperature between 20 and 60° C., or using an inorganic or organic acid such as hydrochloric acid or acetic acid dissolved in an aliphatic alcohol containing 1 to 3 carbon atoms or in an aliphatic ester such as ethyl acetate, isopropyl acetate or n-butyl acetate in the presence of zinc optionally combined with copper, 2) when R₁ represents a t-butoxycarbonyl radical, R₃ and R₄, which may be identical or different, represent an alkyl radical containing 1 to 4 carbon atoms or an aralkyl radical in which the alkyl portion contains 1 to 4 carbon atoms and the aryl portion is preferably an optionally substituted phenyl radical or an aryl, preferably phenyl, radical, or alternatively R₃ represents a trihalomethyl radical or a phenyl radical substituted with a trihalomethyl radical and R₄ represents a hydrogen atom, or alternatively R₃ and R₄ form, together with the carbon atom to which they are attached, a 4- to 7-membered ring, the product of general formula (X) or (XII) is converted in acidic medium to a product of general formula (XI) or (XIII), which is acylated using benzoyl chloride or a reactive derivative of general formula:

R₂—O—CO—X   (XVII)

in which R₂ is defined as above and X represents a halogen atom (fluorine or chlorine) or a residue —O—R₂ or —O—CO—O—R$_2$, in order to obtain a product of general formula (XVI) in which the protecting groups G'$_1$ and, where appropriate, G'$_2$ are replaced, if necessary by hydrogen atoms in order to obtain a product of general formula (III).

The products of general formula (XI) or (XIII), in which G'$_1$ represents a protecting group for the hydroxyl function chosen from 2,2,2-trichloroethoxycarbonyl and 2-(2-trichloromethylpropoxy)carbonyl radicals and G'$_2$ represents an acetyl radical or a protecting group for the hydroxyl function chosen from 2,2,2-trichloroethoxycarbonyl and 2-(2-trichloromethylpropoxy)carbonyl radicals, may be obtained by treating a product of general formula (X) or (XII), in which R$_1$, G$_1$ and G$_2$ are defined as above, R$_3$ and R$_4$, which may be identical or different, represent an alkyl, aralkyl or aryl radical, or alternatively R$_3$ and R$_4$ form, together with the carbon atom to which they are attached, a 4- to 7-membered ring, with an inorganic acid (hydrochloric acid or sulphuric acid) or an organic acid (formic acid) optionally in an alcohol containing 1 to 3 carbon atoms (methanol, ethanol or isopropanol), at a temperature between 0 and 50° C. Preferably, formic acid is used at a temperature in the region of 20° C.

The products of general formula (XI) or (XIII), in which G'$_1$ represents a hydrogen atom and G'$_2$ represents an acetyl radical, may be obtained by treating a product of general formula (X) or (XII), in which G$_1$ represents a silyl radical and G$_2$ represents an acetyl radical, R$_3$ and R$_4$, which may be identical or different, represent an alkyl, aralkyl or aryl radical, or alternatively R$_3$ and R$_4$ form, together with the carbon atom to which they are attached, a 4- to 7-membered ring, with an inorganic acid (hydrochloric acid, sulphuric acid or hydrofluoric acid) or an organic acid (formic acid, acetic acid, methanesulphonic acid, trifluoromethanesulphonic acid or p-toluenesulphonic acid) used alone or mixed, by working in an organic solvent chosen from alcohols, ethers, esters, aliphatic hydrocarbons, halogenated aliphatic hydrocarbons, aromatic hydrocarbons or nitriles at a temperature between −10 and 60° C.

The products of general formula (XI) or (XIII), in which G'$_1$ represents a hydrogen atom and G'$_2$ represents a hydrogen atom or an acetyl radical, may be obtained by treating a product of general formula (X) or (XII), in which G$_1$ represents a protecting group chosen from 2,2,2-trichloroethoxycarbonyl or 2-(2-trichloromethylpropoxy)carbonyl radicals, G$_2$ represents an acetyl radical or a protecting group chosen from 2,2,2-trichloroethoxycarbonyl or 2-(2-trichloromethylpropoxy)carbonyl radicals, R$_3$ represents a trihalomethyl radical or a phenyl radical substituted with a trihalomethyl radical and R$_4$ represents a hydrogen atom, with zinc, optionally combined with copper, in the presence of acetic acid at a temperature between 30 and 60° C., or using an inorganic or organic acid such as hydrochloric acid or acetic acid dissolved in an aliphatic alcohol containing 1 to 3 carbon atoms (methanol, ethanol, propanol or isopropanol) or in an aliphatic ester (ethyl acetate, isopropyl acetate or n-butyl acetate) in the presence of zinc optionally combined with copper.

Acylation of the product of general formula (XI) or (XIII) using benzoyl chloride or a reactive derivative of general formula (XVII) is carried out in an inert organic solvent chosen from esters such as ethyl acetate, isopropyl acetate or n-butyl acetate and halogenated aliphatic hydrocarbons such as dichloromethane or 1,2-dichloroethane in the presence of an inorganic base such as sodium bicarbonate or an organic base such as triethylamine. The reaction is carried out at a temperature between 0 and 50° C., preferably in the region of 20° C.

The possible replacement by hydrogen atoms of the protecting groups G'$_1$ and G'$_2$ in the product of general formula (XVI), when they represent a 2,2,2-trichloroethoxycarbonyl or 2-(2-trichloromethylpropoxy) carbonyl radical, is generally carried out by treatment with zinc, optionally combined with copper, in the presence of acetic acid at a temperature between 30 and 60° C., or using an inorganic or organic acid such as hydrochloric acid or acetic acid dissolved in an aliphatic alcohol containing 1 to 3 carbon atoms (methanol, ethanol or isopropanol) or in an aliphatic ester (ethyl acetate, isopropyl acetate or n-butyl is acetate) in the presence of zinc optionally combined with copper.

The examples which follow illustrate the present invention.

EXAMPLE 1

To a solution of 12.2 g of methyl (4S,5R)-3-tert-butoxycarbonyl-2,2-dimethyl-4-phenyl-5-oxazolidine carboxylate in 130 cm$^3$ of dichloromethane, maintained under an argon atmosphere and with stirring, are added, at a temperature in the region of 20° C., 9.25 g of resublimed iodine, followed by portionwise addition over 5 minutes of 17.2 g of bis(trifluoroacetoxy)iodobenzene. The reaction mixture is subsequently stirred at a temperature in the region of 25° C. for 40 minutes, followed by addition of 130 cm$^3$ of saturated aqueous sodium hydrogen carbonate solution and kept stirring for a further 5 minutes. The aqueous phase, which is separated off after settling, is extracted with twice 100 cm$^3$ of dichloromethane. The organic phases are combined, washed with twice 10 cm$^3$ of distilled water, dried over magnesium sulphate, filtered and then concentrated to dryness under reduced pressure (2.7 kPa) at 40° C. 15.8 g of a yellow oil are obtained, which product is purified by chromatography on 600 g of silica (0.063–0.2 mm) contained in a column of diameter 7 cm, eluting with a cyclohexane/ethyl acetate mixture (75/25 by volume) and collecting 40 cm$^3$ fractions. The fractions containing only the desired product are combined and concentrated to dryness under reduced pressure (2.7 kPa) at a temperature in the region of 40° C. 16.3 g of a yellow oil are obtained, which product is again purified by chromatography on 900 g of silica (0.063–0.2 mm) contained in a column of diameter 7 cm, eluting with a cyclohexane/ethyl acetate mixture (75/25 by volume) and collecting 40 cm$^3$ fractions. The fractions containing only the desired product are combined and concentrated to dryness under reduced pressure (2.7 kPa) at 40° C. 12.1 g of methyl (4S,5R)-3-tert-butoxycarbonyl-2,2-dimethyl-4-(4-iodophenyl)-5-oxazolidinecarboxylate are thus obtained in the form of a yellow oil.

Methyl (4S,5R)-3-tert-butoxycarbonyl-2,2-dimethyl-4-phenyl-5-oxazolidine carboxylate, which may be prepared according to the method described in the Application PCT WO 9209589 for the preparation of ethyl (4S,5R)-3-tert-butoxycarbonyl-2,2-dimethyl-4-phenyl-5-oxazolidine carboxylate, is obtained in the form of a yellow oil, with an optical rotation: $[\alpha]^{20}_D=-8.6$ (c=1.1; CHCl$_3$).

EXAMPLE 2

To a solution of 1.3 g of methyl (4S,5R)-3-tert-butoxycarbonyl-2,2-dimethyl-4-(4-iodophenyl)-5-oxazolidinecarboxylate in 25 cm$^3$ of ethanol is added, at a temperature in the region of 25° C., a solution of 0.35 g of lithium hydroxide hydrate in 8 cm$^3$ of distilled water. The reaction medium is stirred for 30 minutes at a temperature in the region of 25° C. and then concentrated to dryness under reduced pressure (2.7 kPa) at a temperature in the region of 40° C. The evaporation residue is dissolved in 20 cm³ of distilled water and the solution obtained is washed with twice 15 cm³ of diethyl ether, acidified to a pH in the region of 2 by addition of aqueous 1N hydrochloric acid solution and extracted with twice 40 cm³ of ethyl acetate. The organic phases are combined, washed with twice 10 cm³ of distilled water, dried over magnesium sulphate, filtered and then concentrated to dryness under reduced pressure (2.7 kPa) at a temperature in the region of 40° C. 1.3 g of (4S,5R)-3-tert-butoxycarbonyl-2,2-dimethyl-4-(4-iodophenyl)-5-oxzolidinecarboxylic acid are thus obtained in the form of a yellow oil.

EXAMPLE 3

To a solution of 0.805 g of (4S,5R)-3-tert-butoxycarbonyl-2,2-dimethyl-4-(4-iodophenyl)-5-oxazolidinecarboxylic acid in 20 cm³ of anhydrous toluene are added 0.4 g of N,N'-dicyclohexylcarbodiimide, 1.08 g of 4-acetoxy-2α-benzoyloxy-5β,20-epoxy-1,13α-dihydroxy-9-oxo-7β,10β-bis(2,2,2-trichloroethoxy)carbonyloxy-11-taxene and 0.073 g of 4-dimethylaminopyridine. The reaction medium is subsequently heated with stirring for 3 hours at a temperature in the region of 80° C., followed by cooling to a temperature in the region of 20° C. and addition of a mixture of 25 cm³ of dichloromethane and 15 cm³ of saturated aqueous sodium hydrogen carbonate solution. The aqueous phase is separated off after settling and then extracted with 25 cm³ of dichloromethane. The organic phases are combined, washed with twice 10 cm³ of distilled water, dried over magnesium sulphate, filtered and then concentrated to dryness under reduced pressure (2.7 kPa) at 40° C. 2.1 g of a white foam are obtained, which product is purified by chromatography on 70 g of silica (0,063–0.2 mm) contained in a column of diameter 2.5 cm, eluting with dichloromethane and collecting 20 cm³ fractions. The fractions containing only the desired product are combined and concentrated to dryness under reduced pressure (2.7 kPa) at a temperature in the region of 40° C. 1.35 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (4S,5R)-3-tert-butoxycarbonyl-2,2-dimethyl-4-(4-iodophenyl)-5-oxazolidinecarboxylate are thus obtained in the form of a white foam.

A solution of 1.3 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (4S,5R)-3-tert-butoxycarbonyl-2,2-dimethyl-4-(4-iodophenyl)-5-oxazolidinecarboxylate in 20 cm³ of formic acid is stirred for 4 hours at a temperature in the region of 20° C. and then concentrated to dryness under reduced pressure (2.7 kPa) at a temperature in the region of 40° C. The residual solid is dissolved in 75 cm³ of dichloromethane and the solution obtained is then successively washed with 20 cm³ of saturated aqueous ammonium chloride solution and with twice 10 cm³ of distilled water and concentrated to dryness under reduced pressure (2.7 kPa) at a temperature in the region of 40° C. 1.2 g of a white foam are obtained, which product is purified by chromatography on 70 g of silica (0.063–0.2 mm) contained in a column of diameter 2.5 cm, eluting with a dichloromethane/methanol mixture (98/2 by volume) and collecting 20 cm³ fractions. The fractions containing only the desired product are combined and concentrated to dryness under reduced pressure (2.7 kPa) at a temperature in the region of 40° C. 1 g of 4-acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-amino-2-hydroxy-3-(4-iodophenyl)propionate is thus obtained in the form of a white foam.

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-tert-butoxy-carbonylamino-3-(4-iodophenyl)-2-hydroxypropionate may be prepared in the following way:

To a solution of 0.95 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-amino-2-hydroxy-3-(4-iodophenyl)-propionate in 20 cm³ of dichloromethane, maintained under an argon atmosphere and with stirring, is added 0.074 g of sodium hydrogen carbonate, followed by dropwise addition, at a temperature in the region of 20° C., of a solution of 0.216 g of di-tert-butyl dicarbonate in 5 cm³ of dichloromethane. The solution obtained is stirred for 16 hours at a temperature in the region of 20° C., followed by addition of a mixture of 10 cm³ of distilled water and 25 cm³ of dichloromethane. The aqueous phase is separated off after settling and then extracted with 20 cm³ of dichloromethane. The organic phases are combined, washed with twice 5 cm³ of distilled water, dried over magnesium sulphate, filtered and then concentrated to dryness under reduced pressure (2.7 kPa) at 40° C. 1 g of a white foam is obtained, which is purified by chromatography on 90 g of silica (0.063–0.2 mm) contained in a column of diameter 2.5 cm, eluting with a dichloromethane/methanol mixture (99/1 by volume) and collecting 20 cm³ fractions. The fractions containing only the desired product are combined and concentrated to dryness under reduced pressure (2.7 kPa) at a temperature in the region of 40° C. 0.65 g of 4-acetoxy-2α-benzoyloxy-5β,20-epoxy-1-hydroxy-9-oxo-7β,10β-bis-(2,2,2-trichloroethoxy) carbonyloxy-11-taxen-13α-yl (2R,3S)-3-tert-butoxycarbonylamino-3-(4-iodophenyl)-2-hydroxypropionate is thus obtained in the form of a white foam.

A solution of 0.5 g of 4-acetoxy-2α-benzoyloxy-5β,20-epoxy-1-hydroxy-9-oxo-7β,10β-bis-(2,2,2-trichloroethoxy) carbonyloxy-11-taxen-13α-yl (2R,3S)-3-tert-butoxycarbonylamino-3-(4-iodophenyl)-2-hydroxypropionate in a mixture of 10 cm³ of methanol and 10 cm³ of acetic acid is heated, with stirring and under an argon atmosphere, to a temperature in the region of 60° C. and 1 g of zinc powder is then added. The reaction mixture is subsequently stirred for 5 minutes at 60° C. and then cooled to a temperature in the region of 20° C. and filtered through a pad of Celite on a sintered glass funnel. The sintered glass funnel is washed with 3 times 10 cm³ of dichloromethane and the filtrates are combined and then concentrated to dryness under reduced pressure (2.7 kPa) at a temperature in the region of 40° C.

10 cm³ of distilled water is added to the residue and the crystallized solid is separated off by filtration, washed with 5 times 5 cm³ of distilled water and dried under reduced pressure (0.27 kPa) at 20° C. for 16 hours. 0.40 g of a white foam is obtained, which is purified by chromatography on 40 g of silica (0.063–0.2 mm) contained in a column of diameter 2 cm, eluting with a dichloromethane/methanol mixture (97/3 by volume) and collecting 20 cm³ fractions. The fractions containing only the desired product are combined and concentrated to dryness under reduced pressure (2.7 kPa) at 40° C. 0.35 g of a white foam is obtained, which is again purified by chromatography on 70 g of silica (0.063–0.2 mm) contained in a column of diameter 2.5 cm, eluting with a dichloromethane/methanol mixture (97.5/2.5 by volume) and collecting 20 cm³ fractions. The fractions containing only the desired product are combined and concentrated to dryness under reduced pressure (0.27 kPa) at 40° C. for 16 hours. 0.25 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-iodophenyl)-2-hydroxypropionate is thus obtained in the form of a white foam, the characteristics of which are the following:

optical rotation: $[\alpha]^{20}_D$=−33 (c=0.34; methanol)

N.M.R. spectrum: (400 MHz; CDCl$_3$; δ in ppm): 1.15 (s, 3H: —C$\underline{H}_3$ 16 or 17); 1.25 (s, 3H: —C$\underline{H}_3$ 16 or 17); 1.35 [s, 9H: —C(C$\underline{H}_3$)$_3$]; 1.72 (s, 1H: —O$\underline{H}$ 1); 1.78 (s, 3H: —C$\underline{H}_3$ 19); 1.87 [mt,1H: —(CH)—$\underline{H}$ 6]; 1.88 (s, 3H: —C$\underline{H}_3$18); 2.28 (limiting ab, 2H: —C$\underline{H}_2$— 14); 2.39 (s, 3H: —COC$\underline{H}_3$); 2.61 [mt, 1H: —(CH)—$\underline{H}$6]; 3.45 (d,J=4.5 Hz, 1H: —O$\underline{H}$ 2'); 3.92 (d,J=7 Hz, 1H: —$\underline{H}$3); 4.20 (d,J=8 Hz, 1H: —(CH)—$\underline{H}$ 20); 4.23 (broad s, 1H: —O$\underline{H}$ 10); 4.25 (mt, 1H: —$\underline{H}$7); 4.33 [d,J=8 Hz, 1H: —(CH)—$\underline{H}$ 20]; 4.61 (broad s, 1H: —$\underline{H}$2'); 4.96 (broad d,J=10 Hz, 1H: —$\underline{H}$ 5); 5.23 (s, 1H: —$\underline{H}$10); 5.24 (broad d,J=10 Hz, 1H: —$\underline{H}$3'); 5.42 (d,J=10 Hz, 1H: —CON$\underline{H}$); 5.69 (d,J=7 Hz, 1H: —$\underline{H}$ 2); 6.25 (t,J=9 Hz, 1H: —$\underline{H}$ 13); 7.15 and 7.73 [2d,J=8 Hz, 2H each: —C$_6$H$_5$ 3' (—$\underline{H}$ 2, —$\underline{H}$ 3, —$\underline{H}$5 and —$\underline{H}$6)]; 7.50 [t,J=7.5 Hz, 2H: —OCOC$_6$H$_5$(—$\underline{H}$ 3 and —$\underline{H}$ 5)]; 7.62 [t,J=7.5 Hz, 1H: —OCOC$_6$H$_5$(—$\underline{H}$ 4)]; 8.11 [d,J=7.5 Hz, 2H: —OCOC$_6$H$_5$(—$\underline{H}$ 2 and —$\underline{H}$6)].

4-Acetoxy-2α-benzoyloxy-5β,20-epoxy-1,13α-dihydroxy-9-oxo-7β,10β-bis(2,2,2-trichloroethoxy)-carbonyloxy-11-taxene may be prepared under the conditions described in European Patent EP 0,336,841, corresponding U.S. Pat. No. 4,924,012.

EXAMPLE 4

To a solution of 1.43 g of methyl (4S,5R)-3-tert-butoxycarbonyl-2,2-dimethyl-4-(4-iodo)phenyl-5-oxazolidinecarboxylate in 6 cm$^3$ of toluene, maintained under an argon atmosphere and with stirring, is added, at a temperature in the region of 20° C., 0.11 g of tetrakis(triphenylphosphine)palladium, followed by dropwise addition, at a temperature in the region of 20° C., of a solution of 0.44 g of phenylboronic acid in 1.5 cm$^3$ of methanol and a solution of 0.63 g of sodium hydrogen carbonate in 3 cm$^3$ of distilled water. The reaction mixture is subsequently heated, with stirring, for 6 hours at a temperature in the region of 80° C., followed by cooling to a temperature in the region of 20° C. and addition of a mixture of 100 cm$^3$ of ethyl acetate and 15 cm$^3$ of distilled water. The organic phase is separated off after settling, washed with 3 times 5 cm$^3$ of distilled water, dried over magnesium sulphate, filtered and then concentrated to dryness under reduced pressure (2.7 kPa) at 40° C. 1.6 g of a white foam are obtained, which product is purified by chromatography on 90 g of silica (0.063–0.2 mm) contained in a column of diameter 2.5 cm (eluent: dichloromethane), collecting 20 cm$^3$ fractions. The fractions containing only the desired product are combined and concentrated to dryness under reduced pressure (2.7 kPa) at a temperature in the region of 40° C. 1.2 g of methyl (4S,5R)-3-tert-butoxycarbonyl-2,2-dimethyl-4-(4-biphenylyl)-5-oxazolidinecarboxylate are thus obtained, in the form of a yellow oil which is converted to the corresponding acid under the conditions described in Example 2.

EXAMPLE 5

By working as in Example 3, but using 0.55 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-biphenylyl)-2-hydroxypropionate, 0.306 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-biphenylyl)-2-hydroxypropionate in the form of a white foam, the characteristics of which are the following:

optical rotation: $[\alpha]^{20}_D$=−30 (c=0.58; methanol)

N.M.R. spectrum: (400 MHz; CDCl$_3$; δ in ppm): 1.15 (s, 3H: C$\underline{H}_3$ 16 or 17); 1.26 (s, 3H: —C$\underline{H}_3$ 16 or 17); 1.37 [s. 9H: —C(C$\underline{H}_3$)$_3$]; 1.74 (s, 1H: —O$\underline{H}$ 1); 1.78 (s, 3H: —C$\underline{H}_3$ 19); 1.87 [mt,1H: —(CH)—H6]; 1.90 (s,3H: —C$\underline{H}_3$18); 2.27 to 2.35 (2dd,J=17 and 9 Hz, 1H each: —C$\underline{H}_2$— 14); 2.43 (s, 3H: —COC$\underline{H}_3$); 2.60 [mt,1H: —(CH)—$\underline{H}$ 6]; 3.48 (d,J=4.5 Hz, 1H: —O$\underline{H}$2'); 3.94 (d,J=7 Hz, 1H: —$\underline{H}$3); 4.20 (d,J=8 Hz, 1H: —(CH)—$\underline{H}$ 20); 4.24 (broad s, 1H: —O$\underline{H}$ 10); 4.25 (mt,1H: —$\underline{H}$ 7); 4.33 [d,J=8 Hz,1H: —(CH)—$\underline{H}$ 20]; 4.69 (broad s, 1H: —$\underline{H}$2'); 4.96 (broad d,J=10 Hz,1H: —$\underline{H}$ 5); 5.23 (s, 1H: —$\underline{H}$10); 5.34 (broad d,J=10 Hz,1H: $\underline{H}$ 3'); 5.50 (d,J=10 Hz,1H: —CON$\underline{H}$—); 5.69 (d,J=7 Hz,1H: —$\underline{H}$ 2); 6.26 (t,J=9 Hz,1H: —$\underline{H}$ 13); 7.30 to 7.65 (mt, 12H: aromatic —$\underline{H}$); 8.11 [d,J=7.5 Hz,2H: —OCOC$_6$H$_5$($\underline{H}$ 2 and —$\underline{H}$6)].

By working as in Example 3, the following intermediates are prepared from suitable starting materials:

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-tert-butoxycarbonylamino-3-(4-biphenylyl)-2-hydroxypropionate in the form of a white foam.

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-amino-2-hydroxy-3-(4-biphenylyl) propionate in the form of a white foam.

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (4S,5R)-3-tert-butoxycarbonyl-2,2-dimethyl-4 (4-biphenylyl)-5-oxazolidinecarboxylate in the form of a white foam.

EXAMPLE 6

Methyl (4S,5R)-3-tert-butoxycarbonyl-2,2-dimethyl-4-(4-vinylphenyl)-5-oxazolidinecarboxylate may be prepared as described in Example 4 for methyl (4S,5R)-3-tert-butoxycarbonyl-2,2-dimethyl-4-(4-biphenylyl)-5-oxazolidinecarboxylate, but using 2.4 g of methyl (4S,5R)-3-tert-butoxycarbonyl-2,2-dimethyl-4-(4-iodophenyl)-5-oxazolidinecarboxylate and 0.75 g of vinylboronic acid. 1.1 g of methyl (4S,5R)-3-tert-butoxycarbonyl-2,2-dimethyl-4-(4-vinylphenyl)-5-oxazolidinecarboxylate are thus obtained, in the form of a yellow oil which is converted to the corresponding acid under the conditions described in Example 2.

Vinylboronic acid may be prepared according to the method described by J. Braun and H. Normant, Bull. Soc. Chim. Fr., 1966 (8), 2257, the disclosure of which is herein incorporated by reference.

EXAMPLE 7

By working as in Example 3, but using 0.84 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-vinylphenyl)-2-hydroxypropionate, 0.305 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-vinylphenyl)-2-hydroxypropionate is obtained in the form of a white foam, the characteristics of which are the following:

optical rotation: $[\alpha]^{20}_D$=−36 (c=0.53; methanol)

N.M.R. spectrum: (250 MHz; CDCl$_3$.δ in ppm): 1.15 (s, 3H: —CH$_3$ 16 or 17); 1.26 (s, 3H: —CH$_3$ 16 or 17); 1.37 (s, 9H: —C(CH$_3$)$_3$); 1.71 (s, 1H: —OH 1); 1.78 (s, 3H: —CH$_3$ 19); 1.85 (mt, 1H: —(CH)—H6]; 1.88 (s, 3H: —CH$_3$18); 2.30 (limiting ab, 2H: —CH$_2$-14); 2.39 (s, 3H: —COCH$_3$); 2.60 [mt, 1H: —(CH)—H 6); 3.41 (cplx, 1H: —OH 2'); 3.92 (d,J=7 Hz, 1H: —H3); 4.20 (d,J=8 Hz, 1H: —(CH)—H 20); 4.24 (broad s, 1H; —OH in 10); 4.25 (mt, 1H: —H 7); 4.33 [d,J=8 Hz, 1H: —(CH)—H 20]; 4.64 (broad s, 1H: —H2'); 4.96 (broad d, J=10 Hz, 1H: —H 5); 5.23 (s, 1H: —H10); 5.26 (broad d, J=10 Hz, 1H: —H 3'); 5.26 d,J=11 Hz, 1H: —CH=CH(H)(cis)]; 5.43 (d,J=10 Hz, 1H: —CONH—); 5.69 (d,J=7 Hz, 1H: —H 2); 5.76 (d,J=17.5 Hz, 1H: —CH=CH(H)(trans)]; 6.23 (t,J=9 Hz, 1H: —H 13) 6.70 (dd,J=17.5 and 11 Hz, 1H: —CH=CH$_2$); 7.35 and 7.44 [2d,J=8 Hz, 2H each: —C$_6$H$_5$ in 3' (—H 2, —H 3, —H 5 and —H 6)]; 7.50 [t,J=7.5 Hz, 2H: —OCOC$_6$H$_5$(—H 3 and —H 5)]; 7.62 [t,J=7.5 Hz, 1H: —OCOC$_6$H$_5$(—H 4)]; 8.11 [d,J=7.5 Hz, 2H: —OCOC$_6$H$_5$(—H 2 and —H6)].

By working as in Example 3, the following intermediates are prepared from suitable starting materials:

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-vinylphenyl)-2-hydroxypropionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-amino-2-hydroxy-3-(4-vinylphenyl)-propionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (4S,5R)-3-tert-butoxycarbonyl-2,2-dimethyl-4-(4-vinylphenyl)-5-oxazolidinecarboxylate in the form of a white foam.

EXAMPLE 8

Methyl (4S,5R)-3-tert-butoxycarbonyl-2,2-dimethyl-4-(4-isopropenylphenyl)-5-oxazolidinecarboxylate may be prepared under the conditions described in Example 1 for the preparation of methyl (4S,5R)-3-tert-butoxycarbonyl-2,2-dimethyl-4-(4-biphenylyl)-5-oxazolidinecarboxylate, but using 3.0 g of methyl (4S,5R)-3-tert-butoxycarbonyl-2,2-dimethyl-4-(4-iodophenyl)-5-oxazolidinecarboxylate and 0.81 g of isopropenylboronic acid. 2.07 g of methyl (4S,5R)-3-tert-butoxycarbonyl-2,2-dimethyl-4-(4-isopropenylphenyl)-5-oxazolidinecarboxylate are thus obtained, in the form of a yellow oil which is converted to the corresponding acid under the conditions described in Example 2.

Isopropenylboronic acid may be prepared according to the method described by J. Braun and H. Normant, Bull. Soc. Chim. Fr., 1966 (8), 2257.

EXAMPLE 9

By working as in Example 3, but using 1.71 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-isopropenylphenyl)-2-hydroxypropionate, 0.397 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-isopropenylphenyl)-2-hydroxypropionate is thus obtained in the form of a white foam, the characteristics of which are the following:

optical rotation: $[\alpha]^{20}_D$=−34 (c=0.50; methanol)

N.M.R. spectrum: (400 MHz; CDCl$_3$; δ in ppm); 1.15 (s, 3H: —CH$_3$ 16 or 17); 1.26 (s, 3H: —CH$_3$ 16 or 17); 1.37 [s, 9H: —C(CH$_3$)$_3$]; 1.78 (s, 3H: —CH$_3$ 19); 1.87 [mt, 1H: —(CH)—H 6); 1.89 (s, 3H: —CH$_3$18); 2.15 [s, 3H: —C(CH$_3$)=CH$_2$]; 2.26 to 2.34 (2dd,J=16 and 9 Hz, 1H each: —CH$_2$— 14); 2.41 (s, 3H: —COCH$_3$); 2.60 [mt, 1H: —(CH)—H 6); 3.36 (cplx, 1H: —OH 2'); 3.93 (d,J=7 Hz, 1H: —H3); 4.10 to 4.30 (cplx, 1H: —OH in 10); 4.20 (d,J=8 Hz, 1H: —(CH)—H 20); 4.23 (dd,J=11 and 6.5 Hz: —H 7); 4.33 [d,J=8 Hz, 1H: —(CH)—H 20]; 4.64 (broad s, 1H: —H2'); 4.96 (broad d, J=10 Hz, 1H; —H 5); 5.10 to 5.38 [2s, 1H each: —C(CH$_3$)=CH$_2$]; 5.22 (s, 1H: —H10): 5.28 (broad d, J=10 Hz, 1H: —H 3'); 5.41 (d,J=9 Hz, 1H: —CONH—); 5.69 (d,J=7 Hz, 1H: —H 2); 6.24 (t,J=9 Hz, 1H: —H 13); 7.35 to 7.50 [2d,J=7.5 Hz, 2H each: —C$_6$H$_5$ in 3' (—H 2, —H 3, —H 5 and —H6)]; 7.51 [t,J=7.5 Hz, 2H: —OCOC$_6$H$_5$(—H 3 and —H 5)]; 7.62 [t,J=7.5 Hz, 1H: —OCOC$_6$H$_5$ (—H4)]; 8.11 [d,J=7.5 Hz, 2H: —OCOC$_6$H$_5$ (—H 2 and —H6)].

By working as in Example 3, the following intermediates are prepared from suitable starting materials:

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-isopropenylphenyl)-2-hydroxypropionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-amino-2-hydroxy-3-(4-isopropenyl-phenyl)propionate in the form of a white foam.

4-Acetoxy-2α-benzoyloxy-5β,20-epoxy-1-hydroxy-9-oxo-7β,10β-bis (2,2,2-trichloroethoxy)carbonyloxy-11-taxen-13α-yl (4S,5R)-3-tert-butoxycarbonyl-2,2-dimethyl-4-(4-isopropenylphenyl)-5-oxazolidinecarboxylate in the form of a white foam.

EXAMPLE 10

To a solution of 0.07 g of 4-acetoxy-2α-benzoyloxy-5,20-epoxy-1,7β,10β-trihydroxy-9-oxo-11-taxen-13α-yl (2R,3S)-3-tert-butoxycarbonylamino-3-(4-vinylphenyl)-2-hydroxypropionate in 7 cm$^3$ of dichloromethane is added 0.1 cm$^3$ of methanol and the reaction medium is then cooled to a temperature in the region of −75° C. and a gentle stream of ozone is passed through for 2 hours, at a temperature in the region of −78° C. and with stirring, until the blue colour persists. The reaction medium is subsequently stirred at a temperature in the region of −75° C. for 45 minutes while a gentle stream of air is passed through in order to remove the excess ozone, followed by addition of 0.1 cm$^3$ of dimethyl sulphide, warming to a temperature in the region of 20° C. and maintenance at this temperature for 1 hour. The reaction medium is washed with twice 5 cm$^3$ of distilled water, dried over magnesium sulphate, filtered and then concentrated to dryness under reduced pressure (2.7 kPa) at 40° C. 0.05 g of a white foam is obtained, which is purified by chromatography on 30 g of silica (0.063–0.2 mm) contained in a column of diameter 2 cm, eluting with a dichloromethane/methanol mixture (97/3 by volume) and collecting 20 cm$^3$ fractions. The fractions containing only the desired product are combined and concentrated to dryness under reduced pressure (0.27 kPa) at 40° C. for 16 hours. 0.041 g of 4-acetoxy-2α-benzoyloxy-5β,20-epoxy-1,7β,10β-trihydroxy-9-oxo-11-taxen-13α-yl (2R,3S)-3-tertbutoxycarbonylamino-3-(4-formylphenyl)-2-hydroxypropionate is thus obtained in the form of a white foam, the characteristics of which are the following:

optical rotation: $[\alpha]^{20}_{D}=-26$ (c=0.21; methanol)

N.M.R. spectrum: (400 MHz; CDCl$_3$; δ in ppm): 1.16 (s, 3H: —CH$_3$ 16 or 17); 1.26 (s, 3H: —CH$_3$ 16 or 17); 1.37 [s, 9H: —C(CH$_3$)$_3$]; 1.78 (s, 3H: —CH$_3$ 19); 1.87 [mt, 1H: —(CH)—H 6]; 1.88 (s, 3H: —CH$_3$18); 2.30 (limiting ab, 2H: —CH$_2$— 14); 2.41 (s, 3H: —COCH$_3$); 2.61 [mt, 1H: —(CH)—H 6]; 3.94 (d, 1H: —H3); 4.10 to 4.40 (cplx, 1H: —OH in 10); 4.20 (d,J=8 Hz, 1H: —(CH)—H 20); 4.24 (dd,J=12 and 7 Hz, 1H: —H 7); 4.33 [d,J=8 Hz, 1H: —(CH)—H 20); 4.69 (broad s, 1H: —H2'); 4.96 (broad d, J=10 Hz, —H 5); 5.22 (s, 1H: —H10); 5.39 (broad d, J=10 Hz, 1H: —H3'); 5.50 (d,J=10 Hz, 1H: —CONH—); 5.69 (d,J=7 Hz, 1H: —H 2); 6.29 (t,J=9 Hz, 1H: —H 13); 7.50 [t,J=7.5 Hz, 2H: —OCOC$_6$H$_5$(—H 3 and —H 5)]; 7.58 and 7.94 [2d,J=7.5 Hz, 2H each: —C$_6$H$_5$ 3' (—H 2, —H 3, —H 5 and H 6)]; 7.62 [t,J=7.5 Hz, 1H: —OCOC$_6$H$_5$ (—H 4)]; 8.12 [d,J=7.5 Hz, 2H: —OCOC$_6$H$_5$(—H 2 and —H 6)]; 10.04 (s, 1H: —CHO).

EXAMPLE 11

To a solution of 0.28 g of 4-acetoxy-2α-benzoyloxy-5,20-epoxy-1,7β,10β-trihydroxy-9-oxo-11-taxen-13α-yl (2R,3S)-3-tert-butoxycarbonylamino-3-(4-formylphenyl)-2-hydroxypropionate in 15 cm$^3$ of methanol are simultaneously added, with stirring and at a temperature in the region of 20° C., 0.025 g of sodium cyanoborohydride portionwise and 2N hydrochloric acid solution in diethyl ether dropwise in order to maintain the pH at about 6. The reaction medium is subsequently stirred at a temperature in the region of 20° C. for 5 hours and then concentrated to dryness under reduced pressure (2.7 kPa) at 40° C. 0.25 g of a white foam is obtained, which is purified by chromatography on 40 g of silica (0.063–0.2 mm) contained in a column of diameter 2 cm, eluting with a dichloromethane/methanol mixture (97/3 by volume) and collecting 20 cm$^3$ fractions. The fractions containing only the desired product are combined and concentrated to dryness under reduced pressure (2.7 kPa) at 40° C. 0.135 g of a white foam is obtained, which is purified by chromatography on silica gel deposited on a plate (1 cm thick gel; plates of 20×20 cm) in 10 mg fractions. After the area corresponding to the adsorbed desired product is located using U.V. rays, this area is scraped off and the silica recovered is washed on a sintered glass funnel with 10 times 10 cm$^3$ of dichloromethane and with 5 times 5 cm$^3$ of methanol. The filtrates are combined and concentrated to dryness under reduced pressure (0.27 kPa) at 40° C. for 16 hours. 0.077 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-hydroxymethylphenyl)-2-hydroxypropionate is thus obtained in the form of a white foam, the characteristics of which are the following:

optical rotation: $[\alpha]^{20}_{D}=-33$ (c=0.51; methanol)

N.M.R. spectrum: (400 MHz; CDCl$_3$; δ in ppm) 1.13 (s, 3H: —CH$_3$ 16 or 17); 1.22 (s, 3H; —CH$_3$ 16 or 17); 1.37 (s, 9H: —C(CH$_3$)$_3$); 1.75 (s, 3H: —CH$_3$ 19); 1.84 [mt, 1H: —(CH)—H 6]; 1.86 (s, 3H: —CH$_3$18); 2.00 to 2.25 (mt, 2H: —CH$_2$— 14); 2.38 (s, 3H: —COCH$_3$); 2.58 [mt, 1H: —(CH)—H 6]; 3.40 to 3.70 (cplx, 1H: —OH 2'); 3.87 (d,J=7 Hz, 1H: —H3); 4.10 to 4.30 (cplx, 1H: —OH 10) 4.18 (d,J=8 Hz, 1H: —(CH)—H 20); 4.20 (dd,J=11 and 6 Hz, 1H: —H 7); 4.32 [d,J=8 Hz, 1H: —(CH)—H 20); 4.49 and 4.63 (2d,J=13 Hz, 1H each: —CH$_2$OH); 4.56 (broad s, 1H: —H 2'); 4.95 (broad d, J=10 Hz, 1H: —H 5); 5.18 (mt, 1H: —H 3'); 5.20 (s, 1H: —H 10); 5.43 (d,H=10 Hz, 1H: —CON—H); 5,67 (d,J=7 Hz, 1H: —H 2); 6.08 (t,J=9 Hz, 1H: —H 13); 7.30 to 7.45 [mt, 4H: —C$_6$H$_5$ 3' (—H 2, —H 3, —H 5 and —H 6)]; 7.53 [t,J=7.5 Hz, 2H: —OCOC$_6$H$_5$ (—H 3 and —H 5)]; 7.64 [t,J=7.5 Hz, 1H: —OCOC$_6$H$_5$ (—H 4)]; 8.12 [d,J=7.5 Hz, 2H: —OCOC$_6$H$_5$ (—H 2 and —H6)].

EXAMPLE 12

To a solution of 0.33 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-isopropenylphenyl)-2-hydroxypropionate in 15 cm$^3$ of dichloromethane is added 0.07 cm$^3$ of methanol and the reaction medium is then cooled to a temperature in the region of −65° C. and a gentle stream of ozone is passed through for 3 hours, at a temperature in the region of −65° C. and with stirring, until the blue colour persists. The reaction medium is subsequently stirred at a temperature in the region of −65° C. for 1 hour while passing a gentle stream of air through in order to remove the excess ozone, followed by addition of 0.26 cm$^3$ of dimethyl sulphide, warming to a temperature in the region of 20° C. and maintenance of this temperature for 30 minutes. The reaction medium is washed with twice 10 cm$^3$ of distilled water, dried over magnesium sulphate, filtered and then concentrated to dryness under reduced pressure (2.7 kPa) at 40° C. 0.30 g of a yellow oil is obtained, which is purified by chromatography on 20 g of silica (0.063–0.2 mm) contained in a column of diameter 1.5 cm eluting with a dichloromethane/methanol mixture (99/1 by volume) and collecting 10 cm$^3$ fractions. The fractions containing only the desired product are combined and concentrated to dryness under reduced pressure (2.7 kPa) at 40° C. 0.25 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-acetylphenyl)-2-hydroxypropionate is thus obtained in the form of a yellow oil.

EXAMPLE 13

By working as in Example 3, but using 0.54 g of 4-acetoxy-2α-benzoyloxy-5β,20-epoxy-1-hydroxy-9-oxo-7β,10β-bis(2,2,2-trichloroethoxy)carbonyl-11-taxen-13-yl (2R,3S)-3-tert-butoxycarbonylamino-3-(4-acetylphenyl)-2-hydroxypropionate, 0.205 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-acetylphenyl)-2-hydroxypropionate is obtained in the form of a white foam, the characteristics of which are the following:

optical rotation: $[\alpha]^{20}_{D}=-33$ (c=0.53; methanol)

N.M.R. spectrum: (400 MHz; CDCl$_3$; δ in ppm) 1.15 (s, 3H; —CH$_3$ 16 or 17); 1.25 (s, 3H; —CH$_3$ 16 or 17); 1.35 (s, 9H: —C(CH$_3$)$_3$); 1.78 (s, 3H: —CH$_3$ 19); 1.87 [mt, 1H: —(CH)—H 6]; 1.89 (s, 3H: —CH$_3$18); 2.30 (limiting ab, 2H: —CH$_2$— 14); 2.40 (s, 3H: —COCH$_3$); 2.60 [mt, 1H: —(CH)—H 6]; 2.63 [s, 3H: —C$_6$H$_4$ (p—COCH$_3$)]; 3.93 (d,J=7 Hz, 1H: —H3); 4.20 (d,J=8 Hz, 1H: —(CH)—H 20); 4.24 (dd,J=11 and 6 Hz, 1H: —H 7); 4.33 (d,J=8 Hz, 1H: —(CH)—H 20); 4.67 (broad s, 1H: —H2'); 4.96 (broad d, J=10 Hz, 1H: —H5); 5,22 (s, 1H: —H10); 5.35 (broad d, J=10 Hz, 1H: —H 3'); 5.53 (d,J=10 Hz, 1H: CONH—); 5.69 (d,J=7

Hz, 1H: —H 2); 6,27 (t,J=9 Hz, 1H: —H 13); 7.50 [t,J=7.5 Hz, 2H: —OCOC$_6$H$_5$(—H 3 and —H 5); 7.51 and 8.00 [2d,J=7.5 Hz, 2H each: —C$_6$H$_5$ 3' (—H 2, —H 3, —H 5 and —H 6)]; 7.62 [t,J=7.5 Hz, 1H: —OCOC$_6$H$_5$ (—H4)]; 8.11 [d,J=7.5 Hz, 2H: —OCOC$_6$H$_5$ (—H 2 and —H6)].

By working as in Example 3, the following intermediates are prepared from suitable starting materials:

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-acetylphenyl)-2-hydroxypropionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-amino-2-hydroxy-3-(4-acetylphenyl)-propionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (4S,5R)-3-tert-butoxycarbonyl-2,2-dimethyl-4-(4-acetylphenyl)-5-oxazolidinecarboxylate in the form of a white foam.

EXAMPLE 14

To a solution of 2.13 g of methyl (4S,5R)-3-tert-butoxycarbonyl-2,2-dimethyl-4-(4-iodo)phenyl-5-oxazolidinecarboxylate in 25 cm$^3$ of diethylamine, maintained under an argon atmosphere and with stirring, is added, at a temperature in the region of 20° C., 0.12 g of tetrakis (triphenylphosphine)-palladium, followed by 0.933 cm$^3$ of trimethylsilylacetylene and 5 mg of cuprous iodide. The reaction mixture is subsequently stirred at a temperature in the region of 20° C. for 16 hours and then concentrated to dryness under reduced pressure (2.7 kPa) at 40° C. The evaporation residue is dissolved in 150 cm$^3$ of ethyl acetate and, after adding 1 g of ground charcoal, the solution obtained is stirred for 10 minutes, filtered and then concentrated to dryness under reduced pressure (2.7 kPa) at 40° C. The residual oil is again dissolved in 150 cm$^3$ of ethyl acetate and, after washing with 5 times 15 cm$^3$ of distilled water and adding 1 g of ground charcoal, the solution obtained is stirred for 10 minutes, filtered and then concentrated to dryness under reduced pressure (2.7 kPa) at 40° C. 2.2 g of a white foam are obtained, which product is purified by chromatography on 90 g of silica (0.063–0.2 mm) contained in a column of diameter 3 cm (eluent: dichloromethane), collecting 20 cm$^3$ fractions. The fractions containing only the desired product are combined and concentrated to dryness under reduced pressure (2.7 kPa) at a temperature in the region of 40° C. 1.45 g of methyl (4S,5R)-3-tert-butoxycarbonyl-2,2-dimethyl-4-(4-trimethylsilylethynyl)-5-oxazolidinecarboxylate are thus obtained in the form of a yellow oil.

To a solution of 1.4 g of methyl (4S,5R)-3-tert-butoxycarbonyl-2,2-dimethyl-4-(4-trimethylsilylethynylphenyl)-5-oxazolidinecarboxylate in 20 cm$^3$ of ethanol is added dropwise, with stirring and at a temperature in the region of 20 C., a solution of 1.7 g of silver nitrate in a mixture of 2 cm$^3$ of distilled water and 1 cm$^3$ of ethanol. The reaction mixture is subsequently stirred for 2 hours at a temperature in the region of 20° C., followed by dropwise addition of a solution of 2.93 g of potassium cyanide in 3 cm$^3$ of distilled water. Stirring is continued at a temperature in the region of 20° C. for 18 hours and the mixture is extracted with 3 times 50 cm$^3$ of ethyl acetate. The organic phases are combined, washed with 3 times 5 cm$^3$ of distilled water, dried over magnesium sulphate, filtered and then concentrated to dryness under reduced pressure (2.7 kPa) at 40° C. 0.55 g of methyl (4S,5R)-3-tert-butoxycarbonyl-2,2-dimethyl-4-(4-ethynylphenyl)-5-oxzolidinecarboxylate is thus obtained, in the form of a brown oil which is converted to the corresponding acid under the conditions described in Example 2.

EXAMPLE 15

By working as in Example 3, but using 0.63 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-ethynylphenyl)-2-hydroxypropionate, 0.288 g of 4-acetoxy-2α-benzoyloxy-5β,20-epoxy-1,7β,10β-trihydroxy-9-oxo-11-taxen-13α-yl(2R,3S)-3-tert-butoxycarbonylamino-3-(4-ethynylphenyl)-2-hydroxypropionate is obtained in the form of a white foam, the characteristics of which are the following:

optical rotation: $[\alpha]^{20}_D$=−35° (c=0.56; methanol)

N.M.R. spectrum: (400 MHz; CDCl$_3$; δ in ppm) 1.15 (s, 3H: —CH$_3$ 16 or 17); 1.26 (s, 3H: —CH$_3$ 16 or 17); 1.37 (s, 9H: —C(CH$_3$)$_3$); 1.70 (broad s, 1H: —OH 1); 1.78 (s, 3H: —CH$_3$ 19); 1.87 [mt, 1H: —(CH)—H 6]; 1.89 [mt, 3H: —CH$_3$18); 2.29 (limiting ab, 2H: —CH$_2$— 14); 2.38 (s, 3H: —COCH$_3$); 2.60 [mt, 1H: —(CH)—H 6]; 3.10 (s, 1H: —C≡CH); 3,42 (broad s, 1H: —O—H 2'); 3.93 (d,J=7 Hz, 1H: —H 3); 4.20 (d,J=8 Hz, 1H: —(CH)—H 20); 4.23 (mt, 2H: —H 7 and —O—H 10); 4.33 [d,J=8 Hz, 1H: —(CH)—H 20); 4.64 (broad s, 1H: —H2'); 4,96 (broad d, J=10 Hz, 1H: —H 5); 5.22 (s, 1H: —H10); 5.28 (broad d, J=10 Hz, 1H: —H 3'); 5.43 (d,J=10 Hz, 1H: —CONH); 5.69 (d,J=7 Hz, 1H: —H 2); 6.25 (t,J=9 Hz, 1H: —H 13); 7.36 and 7.53 [2d,J=7.5 Hz, 2H each: —C$_6$H$_5$ 3' (—H 2, —H 3, —H 5 and —H 6)]; 7.51 [t,J=7.5 Hz, 2H: —OCOC$_6$H$_5$ (—H 3 and —H 5)]; 7.62 [t,J=7.5 Hz, 1H: —OCOC$_6$H$_5$ (—H 4)]; 8.11 [d,J=7.5 Hz, 2H: —OCOC$_6$H$_5$ (—H 2 and —H6)].

By working as in Example 3, the following intermediates are prepared from suitable starting materials:

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-ethynylphenyl)-2-hydroxypropionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-amino-2-hydroxy-3-(4-ethynylphenyl)-propionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (4S,5R)-3-tert-butoxycarbonyl-2,2-dimethyl-4-(4-ethynylphenyl)-5-oxazolidinecarboxylate in the form of a white foam.

EXAMPLE 16

To a solution of 6 g of methyl (4S,5R)-3-tert-butoxycarbonyl-2,2-dimethyl-4-(4-vinylphenyl)-5-oxazolidinecarboxylate in 150 cm$^3$ of dichloromethane are added 1.34 cm$^3$ of methanol and the reaction medium is then cooled to a temperature in the region of −74° C. and a gentle stream of ozone is passed through for 2 hours, at a temperature in the region of −74° C. and with stirring, until the blue colour persists. The reaction medium is subsequently stirred at a temperature in the region of −74° C. for 1 hour while passing a gentle stream of air through in order to remove the excess ozone, followed by addition of 4.9 cm³ of dimethyl sulphide, warming to a temperature in the region of 20° C. and maintenance at this temperature for 1 hour. The reaction medium is washed with 3 times 30 cm³ of distilled water, dried over magnesium sulphate, filtered and then concentrated to dryness under reduced pressure (2.7 kPa) at 40° C. 6.45 g of a yellow oil are obtained, which product is purified by chromatography on 130 g of silica (0.063–0.2 mm) contained in a column of diameter 3 cm (eluent: dichloromethane), collecting 10 cm³ fractions. The fractions containing only the desired product are combined and concentrated to dryness under reduced pressure (2.7 kPa) at 40° C. 1.99 g of methyl (4S,5R)-3-tert-butoxycarbonyl-2,2-dimethyl-4-(4-formylphenyl)-5-oxzolidinecarboxylate are thus obtained in the form of a yellow oil.

To a solution of 2.1 g of methyl (4S,5R)-3-tert-butoxycarbonyl-2,2-dimethyl-4-(4-formylphenyl)-5-oxazolidinecarboxylate in 25 cm³ of acetic acid are added 1.06 g of sodium perborate hydrate. The reaction medium is heated with stirring to a temperature in the region of 45° C., maintained for 10 hours at this temperature and then cooled to a temperature in the region of 20° C. and concentrated to dryness under reduced pressure (2.7 kPa) at 40° C. The residual oil is dissolved in 75 cm³ of ethyl acetate and the solution obtained is washed with 5 times 5 cm³ of distilled water, dried over magnesium sulphate, filtered and then concentrated to dryness under reduced pressure (2.7 kPa) at 40° C. 2.2 g of methyl (4S,5R)-3-tert-butoxycarbonyl-2,2-dimethyl-4-(4-carboxyphenyl)-5-oxazolidinecarboxylate are thus obtained in the form of a yellow oil.

A solution of 2.15 g of methyl (4S,5R)-3-tert-butoxycarbonyl-2,2-dimethyl-4-(4-carboxyphenyl)-5-oxazolidinecarboxylate in 45 cm³ of anhydrous toluene is heated, with stirring and under an argon atmosphere, to a temperature in the region of 80° C., followed by dropwise addition over 30 minutes of 6 cm³ of N,N-dimethylformamide di-tert-butyl acetal. The reaction medium is subsequently stirred at a temperature in the region of 80° C. for 2 hours and, after cooling to a temperature in the region of 20° C. and addition of 100 cm³ of ethyl acetate, it is washed with twice 25 cm³ of saturated aqueous sodium hydrogen carbonate solution and then with twice 10 cm³ of distilled water, dried over magnesium sulphate, filtered and then concentrated to dryness under reduced pressure (2.7 kPa) at 40° C. 2.5 g of a yellow oil are obtained, which product is purified by chromatography on 80 g of silica (0.063–0.2 mm) contained in a column of diameter 2.5 cm (eluent: dichloromethane), collecting 20 cm³ fractions. The fractions containing only the desired product are combined and concentrated to dryness under reduced pressure (2.7 kPa) at a temperature in the region of 40° C. 2.1 g of methyl (4S,5R)-3-tert-butoxycarbonyl-2,2-dimethyl-4-(4-tert-butoxycarbonylphenyl)-5-oxazolidinecarboxylate are thus obtained in the form of a yellow oil.

EXAMPLE 17

By working as in Example 3, but using 0.485 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-tert-butoxycarbonylphenyl)-2-hydroxypropionate, 0.136 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-tert-butoxycarbonylphenyl)-2-hydroxypropionate is obtained in the form of a white foam, the characteristics of which are the following:

optical rotation: $[\alpha]^{20}_D$=−35 (c=0.46; methanol)
N.M.R. spectrum: (400 MHz; CDCl₃; δ in ppm) 1.16 (s, 3H: —C$\underline{H}$₃ 16 or 17); 1.28 (s, 3H: —C$\underline{H}$₃ 16 or 17); 1.37 [s, 9H: —NHCOOC(C$\underline{H}$₃)₃]; 1.63 [s, 9H: —C₆H₄ (p—COOC(C$\underline{H}$₃)₃]; 1.69 (s, 1H: —O—$\underline{H}$ 1); 1.78 (s, 3H: —C$\underline{H}$₃ 19); 1.87 [mt, 1H: —(CH)—$\underline{H}$ 6]; 1.91 (s, 3H: —C$\underline{H}$₃18); 2.32 (limiting ab, 2H: —C$\underline{H}$₂— 14); 2.38 (s, 3H: —COC$\underline{H}$₃); 2.60 [mt, 1H: —(CH)—$\underline{H}$ 6); 3.38 (broad s, 1H: —O—$\underline{H}$ 2'); 3.95 (d,J=7 Hz, 1H: —$\underline{H}$ 3); 4.17 (broad s, 1H: —O—$\underline{H}$ 10); 4.22 (d,J=8 Hz, 1H: —(CH)—$\underline{H}$ 20); 4.23 (mt, 1H: —$\underline{H}$ 7); 4.32 [d,J=8 Hz, 1H: —(CH)—$\underline{H}$ 20); 4.65 (broad s, 1H: —$\underline{H}$2'); 4.95 (broad d, J=10 Hz, 1H: —$\underline{H}$ 5); 5.22 (s, 1H: —$\underline{H}$10); 5.34 (broad d, J=10 Hz, 1H: —$\underline{H}$ 3'); 5.42 (d,J=10 Hz, 1H: —CON$\underline{H}$—); 5,71 (d,J=7 Hz, 1H: —$\underline{H}$ 2); 6.28 (t,J=9 Hz, 1H: —$\underline{H}$ 13); 7.46 and 8.01 [2d,J=8 Hz, 2H each: —C₆H₅ 3' (—$\underline{H}$ 2, —$\underline{H}$ 3, —$\underline{H}$ 5 and —$\underline{H}$ 6)]; 7.51 [t,J=7.5 Hz, 2H: —OCOC₆H₅ (—$\underline{H}$ 3 and —$\underline{H}$ 5)1; 7.64 [t,J=7.5 Hz, 1H: —OCOC₆H₅ (—$\underline{H}$ 4)]; 8.11 [d,J=7.5 Hz, 2H: —OCOC6H₅ (—$\underline{H}$ 2 and —$\underline{H}$6)].

By working as in Example 3, the following intermediates are prepared from suitable starting materials:

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-3-(4-tert-butoxycarbonylphenyl)-2-hydroxypropionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-amino-2-hydroxy-3-(4-tert-butoxycarbonylphenyl)propionate in the form of a white foam.

4-Acetoxy-2α-benzoyloxy-5β,20-epoxy-1-hydroxy-9-oxo-7β,10β-bis(2,2,2-trichloroethoxy)carbonyloxy-11-taxen-13α-yl (4S,5R)-3-tert-butoxycarbonyl-2,2-dimethyl-4-(4-tert-butoxycarbonylphenyl)-5-oxzolidinecarboxylate in the form of a white foam.

EXAMPLE 18

A solution of 0.55 g of 4-acetoxy-2α-benzoyloxy-5β,20-epoxy-1-hydroxy-9-oxo-7β,10β-bis(2,2,2-trichloroethoxy) carbonyloxy-11-taxen-13α-yl (2R,3S)-3-tert-butoxycarbonylamino-3-(4-carboxyphenyl)-2-hydroxypropionate in a mixture of 9 cm³ of methanol and 9 cm³ of acetic acid is heated, with stirring and under an argon atmosphere, to a temperature in the region of 60° C., followed by addition of 1.1 g of zinc powder. The reaction mixture is subsequently stirred for 30 minutes at 60° C. and is then cooled to a temperature in the region of 20° C. and filtered through a pad of Celite on a sintered glass funnel. The sintered glass funnel is washed with 3 times 10 cm³ of dichloromethane and the filtrates are combined and then concentrated to dryness under reduced pressure (2.7 kPa) at a temperature in the region of 40° C. 10 cm³ of distilled water is added to the residue and the crystallized solid is separated off by filtration, washed with 5 times 5 cm³ of distilled water and dried under reduced pressure (0.27 kPa) at 20° C. for 16 hours. 0.88 g of a white foam is obtained, which is purified by chromatography on 30 g of silica (0.063–0.2 mm) contained in a column of diameter 1.5 cm, eluting with a dichloromethane/methanol mixture (97/3 by volume) and collecting 10 cm³ fractions. The fractions containing only the desired product are combined and concentrated to dryness under reduced pressure (2.7 kPa) at 40° C. 0.26 g of a white foam is obtained, which is purified by chromatography on silica gel deposited on a plate [thickness 0.5 mm; 7 plates of 20×20 cm; eluent: dichloromethane/methanol (80/20 by volume)]. After the area corresponding to the adsorbed desired product has been located by U.V rays, this area is scraped off and the silica recovered is washed on a sintered glass funnel with 10 times 10 cm³ of dichloromethane and with 5 times 5 cm³ of methanol. The filtrates are combined and concentrated to dryness under reduced pressure (0.27 kPa) at 40° C. for 16 hours. 0.177 g of a white foam is thus obtained, which is purified by chromatography on a Whatman $KC_{18}F$ reverse phase deposited on a plate [thickness 0.2 mm; 10 plates of 20×20 cm, eluent: methanol/water (50/50 by volume)]. After the area corresponding to the adsorbed desired product has been located by U.V. rays, this area is scraped off and the reverse phase recovered is washed on a sintered glass funnel with 10 times 10 cm³ of dichloromethane and with 5 times 5 cm³ of methanol. The filtrates are combined and concentrated to dryness under reduced pressure (0.27 kPa) at 40° C. for 16 hours. 0.074 g of 4-acetoxy-2α-benzoyloxy-5β,20-epoxy-1,7β,10β-trihydroxy-9-oxo-11-taxen-13-yl (2R,3S)-3-tert-butoxycarbonylamino-3-(4-carboxyphenyl)-2-hydroxypropionate is thus obtained in the form of a white foam, the characteristics of which are the following:

optical rotation: $[\alpha]^{20}_D = -41$ (c=0.5; methanol)

N.M.R. spectrum: (600 MHz; $CDCl_3$; δ in ppm): 1.04 (s, 3H: —C$\underline{H}_3$ 16 or 17); 1.13 (s, 3H: —C$\underline{H}_3$ 16 or 17); 1.29 (S, 9H: —C(C$\underline{H}_3$)$_3$); 1.64 (s, 3H: —C$\underline{H}_3$ 19); 1.79 (s, 3H: —C$\underline{H}_3$ 18); 1.79 and 2.42 (2 mt, 1H each: —C$\underline{H}_2$ 6); 2.10 to 2.25 (mt, 2H: —C$\underline{H}_2$ 14); 2.30 (s, 3H: —COC$\underline{H}_3$); 3.78 (d,J=7 Hz, 1H: —$\underline{H}$ 3); 4.10 (dd,J=11 and 7 Hz, 1H: —$\underline{H}$ 7); 4.13 and 4.21 (2d,J=8.5 Hz, 1H each: —C$\underline{H}_2$ 20); 4.52 (mt, 1H: —$\underline{H}$ 2'); 4.88 (broad d, J=10 Hz, 1H: —$\underline{H}$ 5); 5.15 (s, 1H: —$\underline{H}$ 10); 5.17 (mt, 1H: —$\underline{H}$ 3'); 5.58 (d,J=7 Hz, 1H: —$\underline{H}$ 2); 6.10 (t,J=9 Hz, 1H: —$\underline{H}$ 13); 6.20 (d,J=10 Hz, 1H: —CON$\underline{H}$—); 7.37 [d,J=8 Hz, 2H: —$C_6H_5$ 3' (—$\underline{H}$ 3 and —$\underline{H}$ 5)]; 7.40 [t,J=7.5 Hz, 2H: —$OCOC_6H_5$(—$\underline{H}$ 3 and —$\underline{H}$ 5)]; 7.52 [t,J=7.5 Hz, 1H: —$OCOC_6H_5$(—$\underline{H}$ 4)]; 7.96 [t,J= 7.5 Hz, 2H: —$OCOC_6H_5$(—$\underline{H}$ 2 and —$\underline{H}$ 6)]; 8.05 [d,J=8 Hz, 2H: —$C_6H_5$ 3' (—$\underline{H}$ 2 and —$\underline{H}$ 6)].

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-tert-butoxycarbonylamino-3-(4-carboxyphenyl)-2-hydroxy-propionate may be prepared in the following way:

To a solution of 1.2 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-amino-2-hydroxy-3-(4-carboxyphenyl)-propionate in 20 cm³ of pyridine, maintained under an argon atmosphere and with stirring, is added dropwise, at a temperature in the region of 20° C., a solution of 0.347 g of tert-butyl 1,2,2,2-tetrachloroethyl carbonate in 2 cm³ of pyridine. The solution obtained is stirred for 24 hours at a temperature in the region of 20° C. and, after addition of 200 cm³ of dichloromethane, is washed with 4 times 10 cm³ of distilled water, dried over magnesium sulphate, filtered and then concentrated to dryness under reduced pressure (2.7 kPa) at 40° C. 1.67 g of a white foam are obtained, which product is purified by chromatography on 50 g of silica (0.063–0.2 mm) contained in a column of diameter 2 cm, eluting with a dichloromethane/methanol mixture (95/5 by volume) and collecting 10 cm³ fractions. The fractions containing only the desired product are combined and concentrated to dryness under reduced pressure (2.7 kPa) at a temperature in the region of 40° C. 0.95 g of a white foam is thus obtained, which product is purified by chromatography on 22 g of silica (0.063–0.2 mm) contained in a column of diameter 2 cm, eluting with a dichloromethane/methanol mixture (99/1 by volume) and collecting 10 cm³ fractions. The fractions containing only the desired product are combined and concentrated to dryness under reduced pressure (2.7 kPa) at a temperature in the region of 40° C. 0.35 g of 4-acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-tert-butoxycarbonylamino-3-(4-carboxyphenyl)-2-hydroxy-propionate is thus obtained in the form of a white foam.

tert-Butyl 1,2,2,2-tetrachloroethyl carbonate may be prepared according to the method described by G. Barcelo et al., Synthesis, 1986, 627–632, the disclosure of which is incorporated herein by reference.

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (2R,3S)-3-amino-2-hydroxy-3-(4-carboxyphenyl)propionate may be prepared in the following way:

A solution of 2.1 g of 4-acetoxy-2α-benzoyloxy-5β,20-epoxy-1-hydroxy-9-oxo-7β,10β-bis-(2,2,2-trichloroethoxy) carbonyloxy-11-taxen-13α-yl (4S,5R)-3-tert-butoxycarbonyl-2,2-dimethyl-4-[α-methyl-(4-methoxy) benzyloxycarbonyl]-5-oxazolidinecarboxylate in 20 cm³ of formic acid is stirred for 5 hours at a temperature in the region of 20° C. and then concentrated to dryness under reduced pressure (2.7 kPa) at a temperature in the region of 40° C. The residual solid is dissolved in 200 cm³ of ethyl acetate and the solution obtained is washed with 10 cm³ of saturated aqueous sodium chloride solution and then with 3 times 10 cm³ of distilled water, dried over magnesium sulphate and concentrated to dryness under reduced pressure (2.7 kPa) at a temperature in the region of 40° C. 1.8 g of a white foam are obtained, which product is purified by chromatography on 54 g of silica (0.063–0.2 mm) contained in a column of diameter 2.5 cm, eluting with a dichloromethane/methanol mixture (95/5 by volume) and collecting 20 cm³ fractions. The fractions containing only the desired product are combined and concentrated to dryness under reduced pressure (2.7 kPa) at a temperature in the region of 40° C. 1.23 g of 4-acetoxy-2α-benzoyloxy-5β,20-epoxy-1-hydroxy-9-oxo-7β,10β-bis-(2,2,2-trichloroethoxy) carbonyloxy-11-taxen-13α-yl (2R,3S)-3-amino-2-hydroxy-3-(4-carboxyphenyl)propionate are thus obtained in the form of a white foam.

4-Acetoxy-2α-benzoyloxy-5β,20-epoxy-1-hydroxy-9-oxo-7β,10β-bis(2,2,2-trichloroethoxy)-carbonyloxy-11-taxen-13α-yl (4S,5R)-3-tert-butoxycarbonyl-2,2-dimethyl-4-[α-methyl-(4-methoxy)-benzyloxycarbonyl]-5-oxazolidinecarboxylate may be prepared in the following way:

To a solution of 1.7 g of (4S,5R)-3-tert-butoxycarbonyl-2,2-dimethyl-4-[α-methyl-(4-methoxy)-benzyloxycarbonyl]-5-oxazolidinecarboxylic acid in 160 cm³ of anhydrous toluene are added 1.17 g of N,N'-dicyclohexylcarbodiimide, 2.54 g of 4-acetoxy-2α-benzoyloxy-5β,20-epoxy-1,13α-dihydroxy-9-oxo-7β,10β-bis(2,2,2-trichloroethoxy)carbonyloxy-11-taxene and 0.173 g of 4-dimethylaminopyridine. The reaction medium is subsequently maintained at a temperature in the region of 20° C. with stirring for 24 hours, followed by addition of a mixture of 25 cm³ of dichloromethane and 10 cm³ of saturated aqueous sodium hydrogen carbonate solution. The aqueous phase is separated off after settling and is then extracted with 25 cm³ of dichloromethane. The organic phases are combined, washed with twice 10 cm³ of distilled water, dried over magnesium sulphate, filtered and then concentrated to dryness under reduced pressure (2.7 kPa) at 40° C. The white foam obtained is purified by chromatography on 200 g of silica (0.063–0.2 mm) contained in a column of diameter 4.5 cm, eluting with a dichloromethane/methanol mixture (99.5/0.5 by volume) and collecting 20 cm³ fractions. The fractions containing only the desired product are combined and concentrated to dryness under reduced pressure (2.7 kPa) at a temperature in the region of 40° C. 3.9 g of a white foam are thus obtained, which product is purified by chromatography on 120 g of silica (0.063–0.2 mm) contained in a column of diameter 3 cm, eluting with a cyclohexane/ethyl acetate mixture (90/10 by volume) and collecting 10 cm³ fractions. The fractions containing only the desired product are combined and concentrated to dryness under reduced pressure (2.7 kPa) at a temperature in the region of 40° C. 2.3 g of 4-acetoxy-2α-benzoyloxy-5β,20-epoxy-1-hydroxy-9-oxo-7β,10β-bis-(2,2,2-trichloroethoxy)carbonyloxy-11-taxen-13α-yl (4S,5R)-3-tert-butoxycarbonyl-2,2-dimethyl-4-[α-methyl-(4-methoxy)benzyloxycarbonyl]-5-oxazolidinecarboxylate are thus obtained in the form of a white foam.

4-Acetoxy-2α-benzoyloxy-5β,20-epoxy-1,13α-dihydroxy-9-oxo-7β,10β-bis(2,2,2-trichloroethoxy)carbonyloxy-11-taxene may be prepared according to the method described in European Patent: EP 0,336,841.

(4S,5R)-3-tert-Butoxycarbonyl-2,2-dimethyl-4-[α-methyl-(4-methoxy)benzyloxycarbonyl]-5-oxazolidinecarboxylic acid may be prepared in the following way:

To a solution of 2.1 g of methyl (4S,5R)-3-tert-butoxycarbonyl-2,2-dimethyl-4-[α-methyl-(4-methoxy)benzyloxycarbonyl]-5-oxazolidinecarboxylate in 55 cm³ of ethanol is added, at a temperature in the region of 25° C., a solution of 0.172 g of lithium hydroxide hydrate in 10 cm³ of distilled water. The reaction medium is stirred for 2 hours at a temperature in the region of 20° and then concentrated to dryness under reduced pressure (2.7 kPa) at a temperature in the region of 40° C. The evaporation residue is dissolved in 20 cm³ of distilled water and the solution obtained is washed with twice 15 cm³ of diethyl ether, acidified to a pH in the region of 2 by addition of aqueous 0.5N hydrochloric acid solution and extracted with twice 100 cm³ of ethyl acetate. The organic phases are combined, washed with twice 15 cm³ of distilled water, dried over magnesium sulphate, filtered and then concentrated to dryness under reduced pressure (2.7 kPa) at a temperature in the region of 40° C. 1.9 g of (4S,5R)-3-tert-butoxycarbonyl-2,2-dimethyl-4-[α-methyl-(4-methoxy)benzyloxycarbonyl]-5-oxazolidinecarboxylic acid are thus obtained in the form of a white foam.

Methyl (4S,5R)-3-tert-butoxycarbonyl-2,2-dimethyl-4-[α-methyl-(4-methoxy)benzyloxycarbonyl]-5-oxazolidinecarboxylate may be prepared in the following way:

To a solution of 2.76 g of methyl (4S,5R)-3-tert-butoxycarbonyl-2,2-dimethyl-4-(4-carboxyphenyl)-5-oxazolidinecarboxylate in 180 cm³ of anhydrous toluene are added 3.01 g of N,N'-dicyclohexylcarbodiimide, 1.11 g of (4-methoxy)phenylethanol and 0.44 g of 4-dimethylaminopyridine. The reaction medium is subsequently kept stirring for 20 minutes at a temperature in the region of 20° C., followed by addition of a mixture of 40 cm³ of dichloromethane and 20 cm³ of distilled water. The aqueous phase is separated off after settling and is then re-extracted with 25 cm³ of dichloromethane. The organic phases are combined, washed with twice 10 cm³ of distilled water, dried over magnesium sulphate, filtered and then concentrated to dryness under reduced pressure (2.7 kPa) at 40° C. 5.77 g of a white foam are thus obtained, which product is purified by chromatography on 300 g of silica (0.063–0.2 mm) contained in a column of diameter 3.2 cm, eluting with a cyclohexane/ethyl acetate mixture (90/10 by volume) and collecting 5 cm³ fractions. The fractions containing only the desired product are combined and concentrated to dryness under reduced pressure (2.7 kPa) at a temperature in the region of 40° C. 2 g of methyl (4S,5R)-3-tert-butoxy-carbonyl-2,2-dimethyl-4-[α-methyl-(4-methoxy)benzyloxycarbonyl]-5-oxazolidinecarboxylate are thus obtained in the form of a yellow oil.

Methyl (4S,5R)-3-tert-butoxycarbonyl-2,2-dimethyl-4-(4-carboxyphenyl)-5-oxazolidinecarboxylate may be prepared in the following way:

To a solution of 2.45 g of methyl (4S,5R)-3-tert-butoxycarbonyl-2,2-dimethyl-4-(4-formyl)phenyl-5-oxazolidinecarboxylate in 30 cm³ of acetic acid are added, at a temperature in the region of 20° C., 1.56 g of sodium perborate hydrate. The reaction medium is subsequently stirred at a temperature in the region of 45° C. for 14 hours and then concentrated to dryness under reduced pressure (2.7 kPa) at 40° C. The residual solid is dissolved in 100 cm³ of ethyl acetate and the solution obtained is washed with twice 10 cm³ of distilled water and then with 250 cm³ of saturated aqueous sodium hydrogen carbonate solution. The aqueous phase is washed with twice 10 cm³ of diethyl ether, acidified with 40 cm³ of aqueous 6N hydrochloric acid solution and then extracted with twice 100 cm³ of ethyl acetate. The organic solutions are combined, dried over magnesium sulphate, filtered and then concentrated to dryness under reduced pressure (2.7 kPa) at 40° C. 1.18 g of methyl (4S,5R)-3-tert-butoxycarbonyl-2,2-dimethyl-4-(4-carboxyphenyl)-5-oxazolidinecarboxylate are thus obtained in the form of a white foam.

Methyl (4S,5R)-3-tert-butoxycarbonyl-2,2-dimethyl-4-(4-formylphenyl)-5-oxazolidinecarboxylate may be prepared in the following way:

To a solution of 7.55 g of methyl (4S,5R)-3-tert-butoxycarbonyl-2,2-dimethyl-4-(4-vinylphenyl)-5-oxazolidinecarboxylate in 190 cm³ of dichloromethane are added 1.7 cm³ of methanol and the reaction medium is then cooled to a temperature in the region of −78° C. and a gentle stream of ozone is passed through for 4 hours, at a temperature in the region of −78° C. and with stirring, until the blue colour persists. The reaction medium is subsequently stirred at a temperature in the region of −78° C. for 1 hour while a gentle stream of air is passed through in order to remove the excess ozone, followed by addition of 6.2 cm³ of dimethyl sulphide, warming to a temperature in the region of 20° C. and maintenance at this temperature for 1 hour. The reaction mixture is washed with twice 5 cm³ of distilled water, dried over magnesium sulphate, filtered and then concentrated to dryness under reduced pressure (2.7 kPa) at 40° C. 8.1 g of a white foam are obtained, which product is purified by chromatography on 400 g of silica (0.063–0.2 mm) contained in a column of diameter 5 cm, eluting with a dichloromethane/methanol mixture (99.5/0.5 by volume) and collecting 100 cm³ fractions. The fractions containing only the desired product are combined and concentrated to dryness under reduced pressure (0.27 kPa) at 40° C. 4.96 g of methyl (4S,5R)-3-tert-butoxycarbonyl-2,2-dimethyl-4-(4-formylphenyl)-5-oxazolidinecarboxylate are thus obtained in the form of a yellow oil.

Methyl (4S,5R)-3-tert-butoxycarbonyl-2,2-dimethyl-4-(4-vinylphenyl)-5-oxazolidinecarboxylate may be prepared according to the method described in Example 6.

What is claimed is:

1. A process for preparing an oxazolidinecarboxylic acid of formula I:

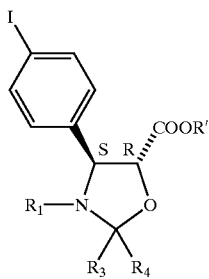

(I)

in which:
R' represents a hydrogen atom, an alkali metal or alkaline-earth metal atom, or an alkyl radical having 1 to 4 carbon atoms,
$R_1$ represents a benzoyl radical or a $R_2$—O—CO— radical in which $R_2$ represents:
a straight or branched alkyl radical having 1 to 8 carbon atoms, an alkenyl radical having 3 to 6 carbon atoms, a cycloalkyl radical having 3 to 6 carbon atoms, or a cycloalkenyl radical having 4 to 6 carbon atoms, these radicals being unsubstituted or substituted with one or more substituents selected from halogen atoms, hydroxyl radicals, alkyloxy radicals having 1 to 4 carbon atoms, dialkylamino radicals in which each alkyl portion has 1 to 4 carbon atoms, piperidino, morpholino and 1-piperazinyl (unsubstituted or substituted at position 4 with an alkyl radical having 1 to 4 carbon atoms radicals, cycloalkyl radicals having 4 to 6 carbon atoms, alkenyl radicals having 4 to 6 carbon atoms, cyano, carboxyl or alkyloxycarbonyl radicals in which the alkyl portion has 1 to 4 carbon atoms; or
alkyl radicals having 1 to 4 carbon atoms, or alkyloxy radicals having 1 to 4 carbon atoms; or
a saturated or unsaturated nitrogen-containing 5- or 6-membered heterocyclic radical unsubstituted or substituted with one or more alkyl radicals having 1 to 4 carbon atoms;
$R_3$ and $R_4$, which may be identical or different, represent:
a hydrogen atom, an alkyl radical having 1 to 4 carbon atoms, an aralkyl radical in which the alkyl portion has 1 to 4 carbon atoms and the aryl portion is substituted with one or more alkoxy radicals having 1 to 4 carbon atoms, or an aryl radical substituted with one or more alkoxy radicals having 1 to 4 carbon atoms; or $R_3$ represents an alkoxy radical having 1 to 4 carbon atoms, a trihalomethyl radical, or a phenyl radical substituted with a trihalomethyl radical and $R_4$ represents a hydrogen atom; or
$R_3$ and $R_4$ form, together with the carbon atom to which they are attached, a 4- to 7-membered ring;
wherein the process comprises a selective iodination carried out on a oxazolidinecarboxylic acid ester of formula II:

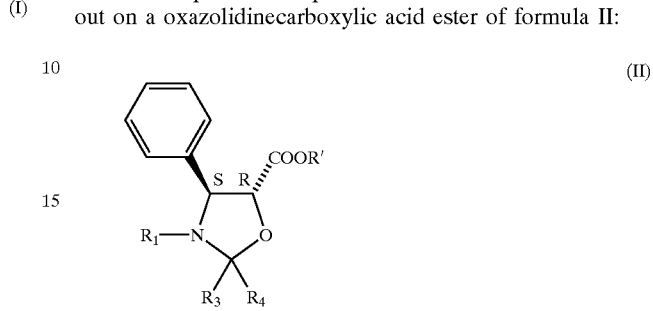

(II)

in which R' represents an alkyl radical having 1 to 4 carbon atoms and $R_1$, $R_3$ and $R_4$ are defined as above.

2. The process according to claim 1, wherein the selective iodination is carried out using iodine and bis(trifluoroacetoxy)iodobenzene.

3. The process according to claim 1, wherein the process is performed in an organic solvent.

4. The process according to claim 3, wherein the organic solvent is a halogenated aliphatic hydrocarbon.

5. The process according to claim 1, wherein the process is performed at a temperature in the range of 0 to 50° C.

6. The process according to claim 1, wherein the selective iodination is carried out using iodine and ammonium cerium nitrate in acetic acid or methanol.

7. The process according to claim 1, wherein the selective iodination is carried out using iodine and silver trifluoroacetate.

8. The process according to claim 1, wherein the selective iodination is carried out using N-iodosuccinimide and hydroxy(tosyloxy)iodobenzene.

9. The process according to claim 1, wherein the selective iodination is carried out using benzyltrimethylammonium dichloroiodide and zinc chloride.

10. The process according to claim 1 wherein the aryl portion of the aralkyl radical is a phenyl radical and the aryl radical is a phenyl radical.

11. The process according to claim 1 wherein the trihalomethyl radical is a trichloromethyl radical.

12. The process of claim 1 wherein the product obtained is saponified.

* * * * *